US008099262B2

(12) United States Patent (10) Patent No.: US 8,099,262 B2
Bacheler et al. (45) Date of Patent: Jan. 17, 2012

(54) ESTIMATION OF CLINICAL CUT-OFFS

(75) Inventors: Lee Terry Bacheler, Chapel Hill, NC (US); Bart Reginald Alfons Winters, Leuven (BE)

(73) Assignee: Virco BVBA, Mechelen (BE)

( * ) Notice: Subject to any disclaimer, the term of this patent is extended or adjusted under 35 U.S.C. 154(b) by 1367 days.

(21) Appl. No.: 10/598,479

(22) PCT Filed: Mar. 1, 2005

(86) PCT No.: PCT/EP2005/050888
§ 371 (c)(1),
(2), (4) Date: Aug. 31, 2006

(87) PCT Pub. No.: WO2005/086061
PCT Pub. Date: Sep. 15, 2005

(65) Prior Publication Data
US 2007/0198232 A1 Aug. 23, 2007

Related U.S. Application Data

(60) Provisional application No. 60/549,219, filed on Mar. 2, 2004, provisional application No. 60/623,481, filed on Oct. 29, 2004.

(51) Int. Cl.
*G06F 17/10* (2006.01)
(52) U.S. Cl. ............................................................ 703/2
(58) Field of Classification Search ........................ 703/2
See application file for complete search history.

(56) References Cited

U.S. PATENT DOCUMENTS

| 6,221,578 B1 | 4/2001 | de Bethune et al. |
| 6,630,343 B1 | 10/2003 | Bartenschlager |
| 7,058,616 B1 | 6/2006 | Larder et al. |

FOREIGN PATENT DOCUMENTS

| EP | 0 945 443 | 9/1999 |
| EP | 1 043 399 | 10/2000 |
| WO | WO 97/08310 | 3/1997 |
| WO | WO 97/27480 | 7/1997 |
| WO | WO 98/39031 | 9/1998 |
| WO | WO 99/37821 | 7/1999 |
| WO | WO 99/67417 | 12/1999 |
| WO | WO 00/27825 | 5/2000 |
| WO | WO 01/79540 | 10/2001 |
| WO | WO 01/95230 | 12/2001 |
| WO | WO 02/33402 | 4/2002 |
| WO | WO 2004/111907 | 12/2004 |

OTHER PUBLICATIONS

Harrigan et al. "World-Wide Variation in HIV-1 Phenotypic Susceptibility in Untreated Individuals: Biologically Relevant Vlaues for Resistance Testing," AIDS (2001) vol. 15, pp. 1671-1677.*
Allison et al., "Osteonecrosis in HIV Disease: Epidemiology, Etiologies, and Clinical Management," *AIDS*, 2003; 17:1-9.
Degruttola et al., "The Relation Between Baseline HIV Drug Resistance and Response to Antiretroviral Therapy: Re-Analysis of Retrospective and Prospective Studies Using a Standardized Data Analysis Plan," *Antiviral Therapy*, 2000; 5:41-48.
Delaney et al., "Cross-Resistance Testing of Antihepadnaviral Compounds using Novel Recombinant Baculoviruses Which Encode Drug-Resistant Strains of Hepatitis B Virus," *Antimicrobial Agents and Chemotherapy*, 2001; 45(6):1705-1713.
Guoming et al., "Resistance of Neisseria Gonorrhoeae Epidemic Strains to Antibiotics," *Sexually Transmitted Diseases*, 2000; 27(2):115-118.
Harrell et al., "Multivariable Prognostic Models: Issues in Developing Models, Evaluating Assumptions and Adequacy, and Measuring and Reducing Errors," *Statist. Med.*, 1996; 15:361-387.
Harrigan et al., "Impact of Moderate Decreases in Baseline NNRTI Susceptibility on Response to Antiretroviral Therapy," $4^{th}$ International Workshop on HIV Drug Resistance and Treatment Strategies, Sitges, Spain, 2000, Abstract 86.
Haubrich et al., "Clinical Utility of Resistance Testing: Retrospective and Prospective Data Supporting Use and Current Recommendations," *Journal of Acquired Immune Deficiency Syndromes*, 2001; 26:S51-S59.
Haubrich et al., "Delavirdine Hypersusceptibility: Virological Response and Phenotypic Cut-Points Results from ACTG 359"; $11^{th}$ Conference on Retroviruses and Opportunistic Infections; Feb. 8-11, 2004, San Francisco, CA USA; Abstract 671.
Hayden et al., "Emergence and Apparent Transmission of Rimantadine-Resistant Influenza A Virus in Families," *New Engl. J. Med.*, 1989; 321:1696-1702.
Iwen et al., "Revised Approach for Identification and Detection of Ampicillin and Vancomycin Resistance in *Enterococcus* Species by Using Micro Scan Panels," *Journal of Clinical Microbiology*, 1996; 34(7):1779-1783.
Japour et al., "Standardized Peripheral Blood Mononuclear Cell Culture Assay for Determination of Drug Susceptibilities of Clinical Human Immunodeficiency Virus Type 1 Isolates," *Antimicrobial Agents and Chemotherapy*, 1993; 37(5):1095-1101.
Katzenstein et al., "Phenotypic Susceptibility and Virological Outcome in Nucleoside-Experienced Patients Receiving Three or Four Antiretroviral Drugs," *AIDS*, 2003; 17:821-830.
Kellam et al., "Recombinant Virus Assay: a Rapid, Phenotypic Assay for Assessment of Drug Susceptibility of Human Immunodeficiency Virus Type 1 Isolates," *Antimicrobial Agents and Chemotherapy*, 1994; 38(1):23-30.
Kusumi et al., "Human Immunodeficiency Virus Type 1 Envelope Gene Structure and Diversity In Vivo and After Cocultivation in Vitro," *Journal of Virology*, 1992; 66(2):875-885.
Lozano-Chiu et al., "Evaluation of a Colorimetric Method for Detecting Amphotericin B-Resistant *Candida* Isolates," *Diagnostic Microbiology and Infectious Disease*, 1998; 31(3):417-424.

(Continued)

*Primary Examiner* — Jerry Lin
(74) *Attorney, Agent, or Firm* — Patton Boggs LLP

(57) ABSTRACT

Methods and systems for improving the accuracy of predicting resistance of a disease to a drug are described. More specifically, methods for assessing the impact of pre-existing variations in drug susceptibility, whether naturally occurring or selected by previous drug exposure, on treatment response in order to establish clinically relevant cut-off values for phenotypic or genotypic resistance tests are described.

21 Claims, 17 Drawing Sheets

OTHER PUBLICATIONS

Pauwels et al., "Comprehensive HIV Drug Resistance Monitoring using Rapid, High-throughput Phenotypic and Genotypic Assays with Correlative Data Analysis," *2nd Int'l Workshop on HIV Drug Resistance and Treatment Strategies*, Lake Maggiore, Italy, 1998; Abstract 51.

Tural et al., "Clinical Utility of HIV-1 Genotyping and Expert Advice: The Havana Trial," *AIDS*, 2002; 16(2):209-218.

International Search Report from PCT/EP2005/050888 dated Oct. 7, 2005, 4 pp.

Bacheler, L. et al., Impact of baseline NNRTI resistance on the efficacy of efavirenz combination therapy in NNRTI therapy-naive patients (study DMP 266006), *Antiviral Therapy*, 2000; 5(Suppl 3):70 [Abstract 88].

Marschall et al., Recombinant Green Fluorescent Protein-Expressing Human Cytomegalovirus as a Tool for Screening Antiviral Agents, *Antimicrobial Agent and Chemotherapy*, 2000; 44(6):1588-1597.

\* cited by examiner

ESTIMATION OF CLINICAL CUT-OFFS

CROSS-REFERENCE TO RELATED APPLICATIONS

This application is a National Stage of International Application No. PCT/EP05/50888, filed Mar. 1, 2005, which claims benefit of U.S. Provisional Application No. 60/549,219, filed Mar. 2, 2004 and U.S. Provisional Application No. 60/623,481, filed Oct. 29, 2004, all of which are incorporated by reference in their entirety.

The present invention concerns methods and systems for improving the accuracy of predicting resistance of a disease to a drug. More specifically, the invention provides methods for assessing the impact of pre-existing variations in drug susceptibility, whether naturally occurring or selected by previous drug exposure, on treatment response in order to establish clinically relevant cut-off values for phenotypic or genotypic resistance tests.

All publications, patents and patent applications cited herein are incorporated in full by reference.

Techniques to determine the resistance of a disease to a drug are becoming increasingly important. Since the issuance of the first report suggesting a correlation between the emergence of viral resistance and clinical progression, techniques to determine the resistance of a pathogen to a drug have been increasingly incorporated into clinical studies of therapeutic regimens (see Brendan Larder et al., HIV Resistance and Implications for Therapy (1998), herein incorporated by reference). For example, as with viral infections, some studies show that p53 mutations may also be predictive of tumour response to specific anticancer drug therapy, radiation treatment or gene therapy. This is the case in breast cancer where initial studies have shown that cisplatin and tamoxifen are more effective in patients whose tumours have a p53 mutation. Thus, the aim of resistance monitoring is to provide the necessary information to enable the physician to prescribe the most optimal combination of drugs for the individual patient.

With more therapeutic options becoming available over time, resistance testing is expected to play an important role in the management and treatment of disease and the development of individualized treatment regimes [see e.g. Haubrich et al. JAIDS, 2001, 26S1, S51-S59].

Furthermore, the number of drug resistant diseases is also increasing. Phenotyping methodologies measure the ability of a pathogen to grow in the presence of different drugs in the laboratory. This is usually expressed as the fold change in the $IC_{50}$ or $IC_{90}$ values (the $IC_{50}$ or $IC_{90}$ value being the drug concentration at which 50% or 90% respectively of the population of pathogen is inhibited from replicating). For example, a highly resistant virus might show a 50 or even 100-fold increase in $IC_{50}$, for example. Some viral mutations only increase the $IC_{50}$ by as little as 2-3 fold. On the other hand, a pathogen may exhibit hypersensitivity towards a given drug. For example, it has been demonstrated that a combination of HIV mutations may lead to hypersensitivity of the pathogen towards a given drug.

Unlike genotyping, phenotyping is a direct measure of susceptibility, reflecting the effects and interactions of all the mutations, known or unknown, on the behaviour of the pathogen population in the presence of a drug.

The utility of drug susceptibility phenotyping is dependent on the "cut-off" value of the fold increase in, for example, the $IC_{50}$ at which a pathogen is considered resistant. The term "cut-off value", as used herein, refers to the threshold change in susceptibility above which a pathogen is classed as having reduced susceptibility for a particular drug. Drug "resistance", as used herein, pertains to the capacity of resistance, sensitivity, susceptibility or effectiveness of the drug against the pathogen.

There has been recent debate regarding the relevance of some cut-off values currently in use. For example, for viral infections, certain groups currently use technical cut-off values, which are usually the same value for each drug-tested and are determined not by clinical criteria but, for example, by the assay variability seen on repetitive testing of a single wild type standard virus. By repeatedly running a test with the standard reference virus, the reproducibility of the test is measured and a cut-off is set at this level, (e.g., a 2.5-fold increase in $IC_{50}$). This provides a cut-off that depends largely on the analytical performance of the assay. This approach suffers from the limitation that it does not consider the population-based variation in drug responsiveness. In addition, such an approach does not account for different responsiveness towards different drug regimens. The limitations of setting a single cut-off for all available drugs in this way is that it tells the clinician very little about the significance of any change in susceptibility reported by a test. Indeed, some virological cut-off values are clearly out of line with known response data. For example, indications of low level resistance to non-nucleotide reverse transcriptase inhibitors (NNRTIs) does not lead to blunted responses to drugs in previously untreated individuals (Harrigan et al., Bacheler et al., 4th International Workshop on HIV Drug Resistance and Treatment Strategies, Sitges, Spain. Abstr. (2000)). Other assays have cut-off values that are primarily based on the reproducibility of the assay, are the same for each drug, or are not related to whether a drug might work against the pathogen in clinical practice and are, therefore, rather arbitrary.

Methods have already been described to develop more meaningful, biologically relevant cut-off values for drugs used in HIV therapy. For example, Virco measured the $IC_{50}$ values for isolates from 1,000 untreated patients as well as many thousands of samples of HIV-1 with no resistance mutations. The average and the range of susceptibility were calculated for each drug. The cut-offs were then set at two standard deviations above the mean. This statistical term means that a test result falling above the cut-off can be said to be above the normal susceptible range with 97.5% confidence (Harrigan et al. World-wide variation in HIV-1 phenotypic susceptibility in untreated individuals: biologically relevant values for resistance testing. 2001. AIDS 15:1671-1677). Since the susceptibility of untreated and un-mutated virus varied considerably from drug to drug, the predicted biological cut-offs are different for each drug.

The use of biological cut-offs has changed the amount of resistance being reported for HIV. For example, the biological cut-off values for the dideoxynucleoside analogues are lower than the cut-offs used previously and, in a study of 5,000 random clinical samples, revealed a higher and more realistic incidence of resistance. Conversely, the cut-offs for the non-nucleoside reverse transcriptase inhibitors are higher than those previously used.

However, although the biological cut-off values are a vast improvement to the arbitrary cut-offs used previously, there are still disparities between these predicted thresholds and the observed fold-resistance above which a clinical response is actually reduced. There is thus a great need for a method that can establish cut-off fold change resistance values that are clinically-relevant.

The present invention provides a solution to these problems, in the form of new methods for assessing the impact of pre-existing variations in drug susceptibility, whether naturally occurring or selected by previous drug exposure, on treatment response in order to establish clinically relevant cut-off values for phenotypic or genotypic resistance tests.

SUMMARY OF THE INVENTION

According to the invention, there is provided a diagnostic method for estimating for a patient the treatment response of a disease caused by a pathogen to a drug, the method comprising:
comparing the fold change resistance value of the pathogen infecting the patient to a clinical cut-off value which is the fold change resistance value at which a clinically relevant variation of clinical response is observed;
wherein the clinical cut-off value is established by modelling the clinical response of a population of patients treated with the drug to the disease caused by the pathogen as a function of the fold change resistance of the pathogen infecting the patients.

According to the invention, a threshold fold-resistance is established, above which a disease is classified as being resistant to a drug in a clinical context. The method models treatment response of the pathogen causing the disease to a particular drug as a function of baseline pathogen load, baseline resistance, baseline activity of co-administered drugs targeted to the pathogen and treatment history. By "baseline pathogen load" is meant the pathogen load of the patient measured at the start of treatment by the drug. By "baseline fold change resistance" is meant the fold change resistance to the candidate drug exhibited by the pathogen infecting the patient at the start of treatment. By "baseline activity of co-administered drugs targeted to the pathogen" is meant the activity against the pathogen of each drug administered in combination with the drug for which the treatment response is being modeled. By "treatment history" is meant the previous drug exposure of the patient (and therefore, the pathogen).

In a preferred embodiment, the cut-off value is determined as a function of treatment response data in treated subjects, considering baseline pathogen load, baseline fold change resistance, baseline activity of co-administered drugs targeted to the pathogen, and treatment history.

This method thus provides a prediction of clinical outcome at different levels of baseline resistance. According to this methodology, treatment outcome (drop in pathogen load and response rate) is modeled by drug as a function of baseline fold change resistance as determined by reference to a system that measures drug resistance phenotype or predicts drug resistance phenotype from pathogen genotype (such as VirtualPhenotype®, Virco). The models take into account effects of co-administered drugs, baseline pathogen load and, optionally, treatment history in order to avoid any bias introduced by imbalances of clinically-important characteristics. From the model, a prediction of outcome can be made at different levels of the baseline fold change resistance of the pathogen.

Using this methodology, fold change resistance values obtained by comparison of genotype with phenotype (for example, VirtualPhenotype®) are linked with clinical outcome. This is a unique approach; other research groups use different approaches whereby particular mutations or actual phenotype results are linked with clinical outcome.

The methodology of the invention is advantageous over those currently used. For example, conventional approaches do not fully account for the population-based variability in drug sensitivity. In the present method, the population may include treatment naïve and treatment experienced patients, and may be a mixed population which is not restricted to, for example, a single gender, age, race or sexual behaviour.

The method of the invention also accounts for the different responsiveness in a population towards different drugs. The drug-specific clinical cut-off values determined by this approach are more reliable parameters in estimating resistant over sensitive strains of pathogen.

The method also allows clinical cut-offs established using the method to be re-calculated depending on the type of population studied, i.e. a paediatric population may have a different clinical cut-off for a particular drug than the adult population for the same drug.

Of particular importance, this methodology allows the determination of clinical cut-offs for all marketed drugs in a uniform, scientific manner on a substantial database using data derived from response to combination therapy. Currently available cut-offs are determined by reference to a limited amount of data and may be inconsistent as they are determined using different approaches.

According to the invention, clinical cut-off values are established by modeling the clinical response of a population of patients treated with the drug to the disease caused by a particular pathogen as a function of the fold change resistance of the pathogen infecting the patients. The fold change resistance for a pathogen may be established using methods known in the art. Briefly, the sensitivity of a patient sample for a particular drug is compared with the sensitivity of a reference sample for that same drug. This may be done by a) determining the sensitivity of a patient sample for the drug; b) determining the sensitivity of a reference sample for the drug; and c) determining the patient fold change resistance from the quotient of the sensitivity obtained in step a) over the sensitivity obtained in b). Examples of preferred methods for performing these steps are described in detail in co-pending applications WO01/79540 and WO02/33402. Equivalent methods will be apparent to the person of skill in the art.

In a preferred embodiment of the invention, the cut-off fold change resistance value is calculated by reference to the log of the pathogen load drop. In such a method, a linear regression analysis is preferably performed using a set of treatment response data from subjects harbouring the pathogen, wherein the log pathogen load drop $\text{LogPL drop}_i$, for the pathogen infecting a patient i, is modelled as the sum of all of the individual contributions for factors that influence pathogen load drop, according to the following equation:

$$\text{LogPLdrop}_i = \beta_0 + \beta_1 \text{Log}(\text{BaselinePL}_i) + \beta_2(\text{PSS}_i) + \beta_3 (1/\text{FC}_i) + \epsilon_i$$

In this equation, $\text{BaselinePL}_i$ represents the pathogen load of the patient measured at the start of treatment by the drug.

$\text{PSS}_i$ is a phenotypic sensitivity score representing the number of active drugs in the background treatment regimen for the patient, excluding the drug whose contribution to treatment response is being modelled.

$\text{FC}_i$ is a baseline fold change resistance.

$\beta_0$ is the intercept.

$\beta_1$ is a coefficient representing the increase in log pathogen load drop per unit increase of the log of the $\text{BaselinePL}_i$. In the case of HIV and HCV infection, baseline $\text{PL}_i$ is readily quantified by validated commercial assays.

$\beta_2$ is a coefficient indicating the increase in log pathogen load drop per unit increase of the number of sensitive drugs in the background treatment regimen.

$\beta_3$ is a coefficient indicating the increase in log pathogen load drop per unit increase of the inverse of $\text{FC}_i$. The value of this coefficient is part of the output of the described model.

$\epsilon_i$ is an error term which represents the difference between the modelled prediction and the experimentally determined measurement.

The coefficients in the linear regression model may be calculated using a computer analysis package such as PROC LIFEREG. PROC LIFEREG is a procedure within the SAS (Statistical Analysis System) software which performs linear regression on censored data. By default, the LIFEREG Procedure computes initial values for the parameters using ordinary least squares (OLS) ignoring censoring. The log-likelihood function is maximized by means of a ridge-stabilized Newton-Raphson algorithm.

PSSi, the phenotypic sensitivity score, represents the number of active drugs in the background treatment regimen for the patient, as predicted from pathogenic genotype by VirtualPhenotype™ or other algorithms or as measured by actual phenotype testing. The purpose of this term is to allow a drug-specific value to be extracted from treatment response data that has been collected for a patient that has received a combination of drugs. In this way, resistance data relevant solely to the particular drug under investigation is extracted. The other drugs are considered the background regimen; this may be different for different patients. It is necessary to analyze patients with different background regimens together as there would not be enough data to do a sound analysis otherwise.

During this analysis it has to be taken into account that different background regimens influence the clinical outcome in a different way. In order to do this, the activities of background drugs are summarised, by determining the number of active drugs, and thus devising a PSS (preferably judged as active according to VirtualPhenotype®). The PSS is then included in the model.

In a preferred embodiment, the PSS may be calculated based on preliminary clinical cut-offs which are determined as described. The concept of PSS is discussed in detail by DeGruttola et al. (Antiviral Therapy 2000; 5:41-48). In addition, the concept of continuous PSS as a variation of PSS is discussed by Allison et al. (AIDS 2003, 17:1-9); Katzenstein et al. (AIDS 2003; 17:821-830); and Haubrich et al. ("Delavirdine Hypersusceptibility (DLV HS): Virological Response and Phenotypic Cut-Points—Results from ACTG 359"; 11th Conference on Retroviruses and Opportunistic Infections held on 8-11 Feb. 2004 in San Francisco, Calif., USA). The PSS may be determined by an iterative process such that the cut-off value is refined to a constant value. In subsequent iterations of the model, PSS scores based on preliminary clinical cut-offs defined in the first iteration of the model may be utilized.

$FC_i$, the baseline fold change, is equivalent to baseline fold change resistance. These terms are used interchangeably herein. This is a patient-specific term and is determined based on a drug susceptibility phenotype test or predicted based on the genotype of the pathogen infecting a particular patient. The phenotype exhibited by the pathogen of this genotype may be predicted in a number of ways; generally, such techniques compare the genotype to phenotype data collected from a group of patients infected with a pathogen of similar genotype. However, this does not change the fact that this fold change resistance is a characteristic of the specific pathogenic strain infecting an individual patient at baseline.

For example, prediction of baseline fold change resistance may exploit rules-based or other less direct systems of determining the drug resistance phenotype of a pathogen. An example of a less direct system is the Virtual Phenotype (Virco, Inc.; WO01/79540). Prediction of baseline fold change resistance may alternatively use other systems for determining phenotype from genotype information, such as neural networks that determine the drug resistance phenotype of a pathogen based on its genotypic information (see, for example, U.S. Pat. No. 7,058,616; WO01/95230. The neural network may be used to identify mutation(s) or mutation patterns that confer resistance to a drug and defines the genetic basis of drug resistance.

$\beta_0$, the intercept, is the estimated log pathogen load drop for a reference group i.e. a theoretical group of patients with a baseline pathogen load of one, an infinite fold change resistance and no sensitive drugs in the background. The purpose of this term is to improve the model fit. If it was not included, the fitted curve would be forced to pass through the origin (zero Log PL drop at zero fold change resistance), which could lead to an unrealistic model.

The error term, $\epsilon_i$, represents the difference between the modelled prediction and the experimentally determined measurement i.e. the difference between the actual response of the patient and the predicted response. As more data are added to the model, additional factors that are relevant to the determination of clinical cut-off values will be added. This will improve the model fit and therefore the error of the prediction will decrease. All the $\beta$ terms are estimated simultaneously by minimizing the error term.

In this methodology of this embodiment of the invention, censoring (pathogen loads beyond the assay range caused by the detection limits of pathogen load kits) affects the results and therefore procedures that take censoring into account are preferably applied. Preferably, censored values are dealt with by attempting to construct a model that is consistent from extrapolations. This model is applicable to any described methodology. Censored values are thus modelled by replacing the censored value by a maximum likelihood estimation, assuming knowledge of the standard deviation of the measurement error. For example, censored values may be dealt with using the PROC LIFEREG pre-programmed procedure in the statistical analysis package SAS that performs analyses with censored values.

An advantage of the linear regression method described above is that quantitative data about changes in pathogen load can be studied because pathogen load is considered as a continuous variable. This therefore takes into account the maximum amount of information present in the data. Estimates are corrected for covariates in the model (for example, background regimen) and therefore, do not suffer from imbalances in the covariates. Conclusions are limited to patients with covariates that are represented in the dataset in the clinical response database.

Other baseline characteristics may be added to the linear regression if relevant, resulting in the addition of new terms in the equation given above. Examples of additional baseline characteristics include the total duration of the previous treatment, and the time at which treatments were administered. For example, estimates can be corrected for duration by adding a term $\beta_4$(Duration) in the model equation given above.

Furthermore, additional factors may be taken into account, including sensitivity score per drug class (in addition to the overall sensitivity score of the background treatment: cPSS), previous exposure to the drug (naïve: Yes or No; naïve to protease inhibitors: Yes or No; naïve to nucleotide RT Inhibitors: Yes or No; and so on). Further examples will be clear to those of skill in the art.

A quadratic term for the cPSS may be added to the model.

The fold change resistance may be transformed before putting it into the model. For example, a power transformation ranging from $FC^{-3}$ to $FC^1$ may be performed on the fold change.

Accordingly, a more general form of the equation presented above may be expressed as:

$$\mathrm{LogPLdrop}_i = \beta_0 + \beta_1 \mathrm{Log}(\mathrm{BaselinePL}_i) + \beta_2(\mathrm{cPSS}_i) + \beta_3 (\mathrm{cPSS}_i)^2 + \beta_4(FC_i)^p + \beta_5(H_5) + \ldots + \beta_n(H_n) + \epsilon_i$$

wherein p is a power transformation (e.g. ranging from −3 to 1) and $H_5$ to $H_n$ are treatment history parameters (e.g. naïve to antiretroviral therapy, naïve to NRTI treatment, etc. . . . ) or parameters describing the background therapy as a function of a certain therapeutic class (e.g. the number of active NRTI's taken concomitantly with the drug under investigation).

An example of characteristics of analysis datasets (8 week outcome) for individual drugs are in the following form:

| | Range (Drug) |
|---|---|
| Median Baseline Viral Load (log) | 3.32 (TDF)-4.71 (boosted IDV) |
| Median background cPSS | 1.34 (ddC)-2.58 (LPV/r) |
| # regimens including the drug | 24 (unboosted APV)-1551 (3TC) |
| % from cohort data | 21% (unboosted APV)-83% (ddI-EC) |
| % with no resistance mutations | 14.5% (boosted APV)-75% (EFV) |

As stated above, the clinical cut-offs determine the fold change resistance with a diminished predicted clinical response to drug. In an alternative to merely classifying pathogens as sensitive or resistant, the method of this aspect of the invention preferably incorporates three classifications, namely "sensitive", associated with maximum response to drug therapy, "intermediate", associated with reduced, but still significant response to drug therapy, and "resistant", associated with little if any response to drug therapy. For example, by one set of definitions relevant for HIV response, "sensitive" may be classified as a predicted pathogen load drop of more than about 0.6 logs, "intermediate resistance" may be classified as a predicted pathogen load drop of between about 0.2 and about 0.6 logs and "resistant" may be classified as a predicted pathogen load drop of less than about 0.2 logs. In another set of definitions, "sensitive" may be classified as a predicted pathogen load drop of between about 0.5 logs and 1.0 logs. Cut-offs calculated using these definitions are highly dependant on covariates.

In a further preferred embodiment of the invention, the cut-off fold change resistance value is calculated by reference to the probability of the pathogen being susceptible to treatment by the drug for the patient, herein termed Prob of success. In such a method, Prob of success is preferably calculated by performing a logistic regression analysis using data from a clinical response dataset, wherein Prob of success is modelled according to the following equation:

$$\text{Prob of success} = \frac{\exp\left(\begin{array}{c}\beta_0 + \beta_1 \text{Log}(BaselinePL_i) + \\ \beta_2(PSS_i) + \beta_3(1/FC_i)\end{array}\right)}{1 + \exp\left(\left(\begin{array}{c}\beta_0 + \beta_1 \text{Log}(BaselinePL_i) + \\ \beta_2(PSS_i) + \beta_3(1/FC_i)\end{array}\right)\right)}.$$

The terms in the equation are the same as those described above for the embodiment of the invention described above.

This method of logistic regression does not suffer from the censoring problem described above for the linear regression model. Furthermore, the probability of success is an intuitive way of interpreting clinical outcome. One disadvantage is that by classifying the pathogen load into successes and failures, part of the information of the continuous variable pathogen load is lost.

Estimates may also be corrected for covariates as for linear regression.

Again, like the method of the first described embodiment of the invention, the method of second described embodiment also preferably incorporates the three classifications, sensitive, intermediate resistant and resistant. On the basis that the maximum effect is defined as the treatment effect at a fold change resistance of approximately 1 fold change or the fold change demonstrated by wild type viral isolates from patients, and the minimum effect is defined as the treatment effect at a very high fold change resistance (i.e. when the curve reaches a plateau), the "effect range" is the difference between the maximum effect and the minimum effect. The maximum effect may be defined as the treatment effect at fold change resistance of between about 0.7 and about 1.2 fold change resistance.

Preferably, a "sensitive" genotype is classified as a predicted treatment effect of more than about 78-85% of the effect range. Preferably, "intermediate resistant" is classified as a predicted treatment effect of between about 15-25% and about 75-85% of the effect range. Preferably, "resistant" is classified as a predicted treatment effect of less than about 15-25% of the effect range. Cut-offs calculated using this method are less dependent on covariates than the method described earlier which uses predicted pathogen load drops. However, the effect range will vary for different covariates.

With this approach, two cutoffs per drug are identified: a "lower" cutoff which represents the fold change at which the response begins to be lost, and an "upper" cutoff which represents the fold change at which the response is essentially gone.

The lower and upper cutoffs may be defined as the fold change with expected log viral load drops of $\geq 0.6$ and $\leq 0.2$ respectively.

The lower and upper cutoffs may be defined as the fold change associated with an expected 20% and 80% decrease respectively of the reference activity of the drug within the regimen.

Accordingly, a first definition (definition 1) of lower and upper cutoffs are the fold changes with expected log viral load drops of $\geq 0.6$ and $\leq 0.2$ respectively.

A second definition (definition 2) of the lower and higher cutoffs are the fold changes associated with an expected 20% and 80% decrease respectively of the reference activity of the drug within the regimen.

A third definition (definition 3) of the cut-off is the fold change that most optimally distinguished between patients with successful and unsuccessful treatments.

In one embodiment of the invention, definition 1 is applied for Tenofovir on a population taking two active drugs besides tenofovir and with a baseline Log(V1) of 4, gives an predicted drop in log viral load of −0.6 at fold change 3.73.

If definition 2 is applied on the linear regression model, the predicted drop in log viral load may be −1.48 at fold change 1, and −0.28 at the maximum fold change. Therefore the effect range may be −0.28+1.48=1.2.20% of this effect range was observed at fold change 5 (and this value was considered as the upper clinical cut-off value). 80% of the effect range was observed at fold change 1.25 (and this value was considered as the lower clinical cut-off value).

For this embodiment, when the FC of patient is 0.8 (below the lower clinical cut-off), a normal clinical response is predicted. If the FC of the patient is 2 (above the lower clinical cut-off and below the upper clinical cut-off), a reduced clinical response is predicted. If the FC is 7 (above the clinical cut-off), then the clinical response is predicted as being minimal.

In an embodiment when definition 2 is applied, and the logistic model is used for tenofovir, a lower cut-off at 1.2 FC and a higher cut-off at 3.81 FC are determined.

The following table depicts a number of embodiments of the invention for tenofovir for a population with 2 active drugs in the regimen and a baseline Log(VL) of 4.

| Definition of Clinical cut-off | Population | Properties of the subgroup | Linear Regression | | Logistic Regression | | Classification Tree | |
|---|---|---|---|---|---|---|---|---|
| | | | Lower CO | Higher CO | Lower CO | Higher CO | Lower CO | Higher CO |
| Definition 1 | Subgroup 1 | PSS = 2, baseline Log (VL) = 4 | 3.73 | >assay limit | NA | NA | NA | NA |
| | Subgroup 2 | PSS = 0, baseline Log (VL) = 4 | 1.68 | 3.8 | NA | NA | NA | NA |
| | Subgroup 3 | PSS = 2, baseline Log (VL) = 5 | >assay limit | >assay limit | NA | NA | NA | NA |
| | Overall | | NA | NA | NA | NA | NA | NA |
| Definition 2 | Subgroup 1 | PSS = 2, baseline Log (VL) = 4 | 1.25 | 5 | 1.2 | 3.81 | NA | NA |
| | Subgroup 2 | PSS = 0, baseline Log (VL) = 4 | 1.25 | 5 | 1.16 | 3.36 | NA | NA |
| | Subgroup 3 | PSS = 2, baseline Log (VL) = 5 | 1.25 | 5 | 1.17 | 3.4 | NA | NA |
| | Overall | | 1.25 | 5 | NA | NA | NA | NA |
| Definition 3 | Subgroup 1 | PSS = 2, baseline Log (VL) = 4 | 1.1 | 5 | 1.2 | 3.81 | 1.15 | NA |
| | Subgroup 2 | PSS = 0, baseline Log (VL) = 4 | 1.1 | 5 | 1.2 | 3.36 | 1.15 | NA |
| | Subgroup 3 | PSS = 2, baseline Log (VL) = 5 | 1.1 | 5 | 1.2 | 3.4 | 1.15 | NA |
| | Overall | | 1.1 | 5 | 1.2 | NA | 1.15 | NA |

NA: Not Applicable

In a further embodiment, applying definition 1 on the linear regression model for patients with a log baseline viral load of 5 and all patients taking two active drugs in addition to d4T (stavudine), a viral load drop of more than 0.6 log copies/mL for any fold change of d4T is predicted. The viral load drop is predicted to be −0.6 logs and −0.2 logs at fold changes 2.6 and 4.0 for patients with a log baseline viral load of 5 and taking no active drugs in addition to d4T.

In another embodiment, lower and upper cutoffs predicted using definition 2 for lopinavir/r are 8 and 69 respectively for the whole population if viral load is modeled using linear regression, and the lower and upper cutoffs are 11 and 64, 10 and 60, and 9 and 58 respectively for populations with log baseline VL/background PSS of 4/2, 5/0 and 5/2 respectively if the failure rate is modeled using logistic regression.

In another embodiment, lower and upper cutoffs determined using definition 2 for boosted saquinavir for the logistic model are 1.7 and 13.2, and 1.7 and 12.9 respectively for populations with log baseline viral load/phenotypic sensitivity score for the background regimen of 4/2 and 5/0 respectively. In the same circumstances lower and upper cutoffs by linear regression for saquiavir/r are 1.6 and 12.3 respectively for the whole population.

The following table shows a number of embodiments modelled using a preliminary linear regression analysis and definition 2:

| DRUG | VIROLOGIC RESPONSE | |
|---|---|---|
| | Baseline FC for 20% REDUCTION of response (lower cutoff) | Baseline FC for 80% REDUCTION of response (upper cutoff) |
| AZT zidovudine | 1.8 [1.5-2.5] | 17 [10-25] |
| 3TC lamivudine | 1.1 [1.1-1.2] | 2.6 [1.9-4.6] |
| D4T stavudine | 1.3 [1.2-1.4] | 3.4 [3.1-3.6] |
| DdI didanosine (extended release) | 1.3 [1.2-1.9] | 3.6 [2.8-4.9] |
| ABC abacavir | 1.6 [1.1-2.6] | 5.8 [1.7-7.4] |
| TDF Tenofovir | 1.2 [1.1-1.5] | 2.5 [1.7-3.8] |
| IDV indinavir | 1.2 [1.1-1.9] | 3.4 [1.9-16.4] |
| IVD/r Indinavir/r | 3.5 [1.1-8.4] | 25 [1.8-31] |
| NFV nelfinavir | 1.1 [1.1-1.3] | 2.2 [1.7-5.3] |
| SQV saquinavir | 1.1 [1.1-2.1] | 2.0 [1.7-18] |
| SQV/r Saquinavir/r | 1.6 [1.3-4.8] | 12 [5.8-27] |
| AMP amprenavir | 1.2 [1.1-2.4] | 3.4 [1.7-10.2] |
| AMP/r amprenavir/r | 1.5 [1.2-2.6] | 6.8 [3.6-10.5] |
| LPV/r Lopinavir/r | 6.9 [2.1-17.4] | 56 [29-67] |

The values between brackets in the table are the 90% confidence limits as determined by bootstrapping.

In another embodiment, lower clinical cutoffs modelled using definition 2 after 8 weeks were 1.1 to 1.2 for unboosted PIs, and upper clinical cutoffs were 2.0-3.4 for unboosted PIs. Clinical cutoffs for boosted PIs were higher: lower CCO—1.5-6.9 and upper CCO 6.8-56.

In an example for D4T the linear regression model comprises:

$$VLdrop = 2.91 - 0.63 Log(BaselineVL) - 1.66(FC^{0.6}) - 0.99(cPSS) + 0.15(cPSS^2) - 0.18(PSS[NRTI]) + 0.91(NRTI[naïve]).$$

The coefficients in the linear regression model were calculated using PROC LIFEREG.

The NRTI[naïve] value represents whether the patient is naïve to nucleoside RT inhibitors. If yes, value=1, if no, value=0. The PSS[NRTI} represents the phenotypic sensitivity score for NRTIs, i.e the number of active NRTIs in the background regimen for the patient.

When Log(BaselineVL)=4, lower reference fold change=0.9 and upper reference fold change=3, cPSS=2, PSS [NRTI]=1 and NRTI[naïve]=0, the modelled lower and upper CCOs are modeled as 1.1 and 2.2 respectively using definition 2.

In another example, the linear regression model is applied to an 8 week viral load response and modelled as a function of baseline phenotypic resistance. The subjects may have a log baseline viral load=4.0 and a cPSS score for the background regimen of 2.0.

In a further preferred embodiment of the invention, the cut-off fold change resistance value is calculated by constructing a classification tree in order to classify the likelihood of a patient having an undetectable pathogen load after treatment with a particular drug, as a success or a failure. This methodology constructs tree-structured rules in order to classify patients as successes (undetectable pathogen load after treatment) and failures. For example, for a virus an undetectable pathogen load could be defined as a viral load of less than 400 viral copies per ml. Such a classification tree has the advantage that it is very visual and easy to interpret, although it suffers from the limitation that the decisions do not take into account the value of certain other relevant parameters. Imbalances for such parameters may therefore influence the decision taken for a certain parameter. However, such trees provide insights into the importance of several parameters and this can be helpful in the fitting process of the linear regression and logistic regression approaches described above.

The classification tree poses queries, in which the answer to each query results in either the left or the right branch of the tree being taken at each stage. For example, the first query may preferably consider the fold change resistance of the pathogen genotype to the drug in question e.g. is fold change for the drug TDF (tenofovir)<1.35? If yes, the left branch is taken, if no the right branch is taken. As with the methods of the aspects of the invention described previously, the other factors queried include the log baseline pathogen load and the phenotypic sensitivity score. The numbers at the termini of the final branches represent the response rate (1=100% response). Examples of classification trees according to the invention are provided in FIGS. 8a, b and c.

In this embodiment of the invention, the clinical cut-off is defined as the fold change resistance threshold value that makes the best distinction between successful and unsuccessful treatments i.e. the most suitable value posed in the query that bifurcates the tree into the left and right branches. The population is thus split into two subgroups: one with a high success rate and one with a low success rate. The clinical cut-off is chosen as the fold change that makes the difference between the two groups as large as possible.

Preferably, two or all three of the methods of the above-described embodiments of the invention are performed for each dataset and candidate drug. The clinical cut-offs can in this manner be calculated for each of the approaches. From the analysis results, the most appropriate values for lower and higher cut-offs are selected, taking into account the advantages and the disadvantages of the separate approaches. This selection will only be made if the results of the approaches are consistent or if possible inconsistencies can be explained. If there are unexplained inconsistencies between the results, it can be concluded that more data need to be gathered before a clinical cut-off can be determined.

For example, if the results of the different approaches are consistent (preferably clinical cut-off difference<0.5) then the predictions are deemed to be consistent. If the results differ more than that, the disparities need to be explained. For example, if we suppose that the population contains 90% censored values and the linear regression gives a clinical cut-off of 0.9 while the logistic regression gives a clinical cut-off of 3.5, then in this example the linear regression results are less reliable because too much correction has to be made for censoring and there is too little information contributed by "complete" observations.

The models may be validated using bootstrapping or by repeating the described steps several times.

Alternatively, the model may be validated by calculating a concordance index (c-index) (Harrell F. E., Lee K. L. and Mark D. B.—Multivariable prognostic models: issues in developing models, evaluating assumptions and adequacy, and measuring and reducing errors—Statist. Med. 1996; 15:361-357) which describes how all the models can discriminate between patients with a different response.

This c-index may be calculated on the data set used for model development and on a further test data set. If the difference between the two c-indices is small, it means that the models do not lose their predictive ability if applied to new data.

Further factors which may be taken into account when validating the model are the odds ratios determined using clinical cutoffs compared to those determined using biological cutoffs. These ratios represent the odds of being a responder in the group that is labeled resistant by the cutoffs divided by the odds of being a responder in the group that is labeled sensitive by the cutoffs. In this way it is possible to evaluate how well the cutoffs perform on a drug by drug basis. The further away that the odds ratio is from 1, the stronger the correlation between the resistance class and clinical outcome. The odds ratio as specified above yield numbers smaller than 1 as the odds of being a responder should be smaller in the higher resistance class. Put another way, the probability of response will decrease as the resistance increases. Additionally, if the odds ratio for the CCO is smaller than the odds ratio for the BCO, it can be concluded that the CCO is stronger correlated with clinical outcome and therefore gives a better prediction than the BCO.

It is also possible to study the difference in response rate for patients taking 1 active drug more vs. patients taking one active drug less. This, different type of odds ratio is the ratio of odds of response for people taking more active drugs over the odds for people taking less active drugs. In this case, the odds ratio should be >1 as the probability of response will increase as the number of active drugs taken increases. In this case, a larger odds ratio indicates a stronger correlation with clinical outcome. In one dataset, using the CCOs set out on page 36 herein, the odds ratio for response per additional active drug added was 3.01 when calculated using clinical cutoffs, and 2.32 when calculated using biological cutoffs.

A logistic regression model may be used to determine the odds ratio. The model used is the same as the logistic regression model described above except that the fold change in the model is replaced by the resistance class. The coefficient for the resistance class that is obtained from the model is the log (odds ratio). The advantage of using this model is that the odds ratio estimates can be adjusted for the baseline viral load and the cPSS score of the background regimen.

A number of embodiments are shown in the following table which gives values for lower and upper cutoffs with confidence intervals modelled using definition 2 and a linear regression model for several drugs, and validated using C-indices, and CCO odds ratios.

| Drug | Modelled Lower Cutoff & 95% Confidence Interval | Modelled Upper Cutoff & 95% Confidence Interval |
|---|---|---|
| AZT | 1.9 [1.52-2.76] | 14.4 [8.24-21.20] |
| 3TC | 1.1 [0.98-1.39] | 3.7 [1.71-11.44] |

-continued

| Drug | Modelled Lower Cutoff & 95% Confidence Interval | Modelled Upper Cutoff & 95% Confidence Interval |
|---|---|---|
| D4T | 1.1 [1.05-1.12] | 2.2 [2.05-2.30] |
| DDIE | 1.3 [1.07-1.34] | 3.0 [2.59-2.96] |
| ABC | 0.8 [0.75-1.72] | 1.2 [1.19-5.11] |
| TDF | 1.0 [0.97-1.32] | 2.0 [1.51-2.95] |
| NVP | 1.5 [1.40-16.74] | 3.2 [2.22-63.06] |
| EFV | 1.8 [1.41-3.74] | 29.2 [6.46-146.69] |
| IDV | 0.8 [0.77-1.04] | 2.2 [1.33-7.19] |
| IDV/r | 4.1 [0.77-6.24] | 21.2 [1.41-22.86] |
| APV | 0.7 [0.65-0.87] | 1.4 [1.03-5.55] |
| APV/r | 0.9 [0.80-2.72] | 6.5 [4.06-16.22] |
| NFV | 1.0 [0.97-1.03] | 1.5 [1.54-2.38] |
| SQV | 0.7 [0.65-2.28] | 1.0 [1.03-22.61] |
| SQV/r | 1.1 [0.81-5.98] | 12.0 [4.50-28.85] |
| LPV/r | 10.3 [1.53-17.30] | 61.6 [21.92-66.96] |

The methods of the invention can be repeated for each possible drug or therapeutic agent known or suspected to be associated with disease resistance, or towards which a resistance can be expected to appear. As such, according to another embodiment of the invention, the clinical cut-offs generated can be presented as a list of cut-offs against or in respect of individual drugs or individual therapeutic agents, for each pathogen.

As used herein, the term "drug" includes, but is not limited to, a pharmaceutical, bactericide, fungicide, antibiotic, or anticancer, antiviral, anti-bacterial anti-fungal, anti-parasitical or any other compound or composition that can be used in therapy or therapeutic treatment.

A "patient" may be any organism, particularly a human or other mammal, suffering from a disease or in need or desire of treatment for a disease. A patient includes any mammal, including farm animals or pets, and includes humans of any age or state of development. A group of patients useful to establish treatment response as a function of the distribution of fold change resistances may be as low as 10 to 50 patients, 50 to 500 patients, or, more preferably, will comprise a population of 500 or more patients. The distribution fold change resistances can be a normal distribution (Gaussian distribution) or can be a non-normal distribution. The non-normal distribution may be transformed to obtain a normal distribution.

The patient samples may be from treatment naïve or treatment experienced subjects, with or without resistance to one or more drugs.

As used herein, the term "disease" refers to a disease caused by infection with a pathogen. The term "pathogen", as used herein, is used broadly and refers not just to pathogenic microorganisms, but includes any disease-causing agent. Examples include bacteria, viruses such as human immunodeficiency virus (HIV), hepatitis C (HCV) or hepatitis B (HBV), prions, algae, fungi, protozoa and malignant cells. This invention is particularly useful for viral diseases such as HIV.

A "patient sample" is herein defined as any sample obtained from an individual suffering from or predicted to be suffering from a disease caused by a pathogen, and includes tissues such as blood, serum plasma, urine, saliva, semen, breast milk, faeces, mucous samples, cells in cell culture, cells which may be further cultured, biopsy samples and so on. In one embodiment, for a patient infected with HIV, any biological sample-containing virus may be used. Of this patient sample, the pathogen itself may be used or alternatively a protein, or nucleic acid derived from the pathogen. Preferably, the pathogen is a virus, such as a retrovirus. Preferably the biological sample contains a virus chosen from HIV, HCV (Hepatitis C Virus) and HBV (Hepatitis B virus). In another embodiment, for a cancer patient, the patient sample may contain cells, tissue cells, mutated cells, malignant cells, cancer cells, whole or partial tumours, biopsy tissue, etc. Preferably, the pathogen is a malignant cell. A "reference sample" is defined as a standard laboratory reference pathogen such as, for example, in the case of HIV, the HIV LAI IIIB strain. One strain generally used as the reference "wild type" sequence for HIV is HXB2. This viral genome comprises 9718 bp and has an accession number in Genbank at NCBI M38432 or K03455 (gi number: 327742). Reference or wild type sequences for use in the invention in the field of specific diseases, infections or diseases caused by specific pathogens can be easily obtained from publicly available databases.

"Susceptibility" or "sensitivity" to a drug refers to the capacity of the disease, and/or pathogen to be affected by the drug. "Resistance" refers to the degree to which the disease and/or pathogen is unaffected by the drug. The sensitivity, susceptibility or resistance of a disease towards a drug may be expressed by means of an $IC_{50}$ value. The $IC_{50}$ value is the concentration at which a given drug results in a reduction of the pathogen's growth compared to the growth of the pathogen in the absence of a drug. Resistance of a disease to a drug may be caused by alterations in phenotype or genotype. Genotypic alterations include mutations, single nucleotide polymorphisms, microsatellite variations, and/or epigenetic variations such as methylation. Phenotypic variations may be effected by genotypic variations or by post-translational modification.

Any method capable of measuring changes in the ability of a pathogen to grow in the presence of a drug(s) can be used in the method of the present invention. Such methods of phenotyping include all methods known to persons of skill in the art. Known genotyping methods may also be applicable.

For example, and by way of illustration, methods for phenotyping bacteria suitable for use in the present invention include, but are not limited to, measurement of inhibitory zone diameters (see, e.g., Guoming et al., Sex Transm. Dis. 27 (2): 115-8 (2000)), colorimetric indicator methods (see, e.g., Lozano-Chiu et al., Diagn Microbiol Infect Dis. 1998 July; 31(3):417-24), and broth macrodilution method (see, e.g., Iwen et al., J. Clin. Microbiol. 34 (7): 1779-83 (1996)).

As an additional illustrative example, methods for phenotyping pathogens suitable for use in the present invention include, but are not limited to, plaque reduction assays, PBMC p24 growth inhibition assays (see, e.g., Japour et al., Antimicrob Agents Chemother. 1993 May; 37(5):1095-101; Kusumi et al., J. Virol. 66: 875-885 (1992)), recombinant virus assays (see, e.g., Kellam & Larder, Antimicrob. Agents Chemother. 38: 23-30 (1994); and Pauwels et al., 2nd International Workshop on HIV Drug Resistance and Treatment Strategies, Lake Maggiore, Italy. Abstr. 51 (1998)); the use of GFP as a marker to assess the susceptibility of anti-viral inhibitors (Marschall et al., Institute of Clin. and Mot. Virol., University of ErlangerNuremberg, Schlobgarten, Germany); and cell culture assays (Hayden et al., N. Eng. J. Med. 321: 1696-702 (1989)).

Though the invention may be used with any phenotype or genotype measuring test or assay that determines resistance, the following descriptions are designed to describe further possible applications of the invention.

In one embodiment, the clinical cut-off values may be used in concert with direct phenotype assays, for example, Antivirogram™ (Virco, Inc.; WO 97/27480, U.S. Pat. No. 6,221,578). This assay is a phenotypic resistance assay that measures, in controlled laboratory conditions, the level of resistance of the HIV derived from an individual patient to each of the anti-HIV drugs currently available. The resistant "behaviour" of the virus may be the combined result of the effects of many different mutations and the complex interactions between them, including genetic changes that have not even been identified yet. In other words, it is a direct measure of resistance.

The test provides a quantitative measure of viral resistance to all the available drugs. This is expressed in terms of the $IC_{50}$. This is then compared to the $IC_{50}$ for fully sensitive, non-mutated "wild-type" virus. The resistance of the sampled virus to each drug is then expressed in terms of a fold-change in $IC_{50}$ compared to wild type.

The addition of "clinical cut-offs", as described in this application, to the report enables physicians to identify the drug(s) that are no longer clinically active and helps in the selection of the optimal combination of drugs for the individual patient. In one embodiment, the method of the present invention concerns a diagnostic tool for determining the resistance of a patient to at least one HIV drug comprising the clinical cut-off fold change resistance value for said at least one drug as determined herein. The diagnostic tool includes phenotypic resistance tests such as the Antivirogram®, VirtualPhenotyping® and Phenosense.

The invention includes methods to deter line resistance towards HIV compounds such as tenofovir, lopinavir, and those compounds disclosed in WO99/67417, EP-A-945443 and WO00/27825. Other examples of drugs will be well known to those of skill in the art.

In one embodiment the effect of drugs on HBV may be monitored using technologies such as disclosed by Isom et al. (WO 99/37821, Delaney et al. Antimicrob. Agents Chemotherap. 2001, 45 (6) 1705-1713).

In one embodiment the effect of drugs on HCV towards therapy may be determined using techniques such as described by Rice (WO 97/08310, WO 98/39031) and Barthenschlager (EP 1043399).

The primary aim of the invention is to predict the resistance of a disease to a particular drug. In addition, however, the invention encompasses methods of evaluating currently applied drugs and thus monitoring these drugs with a view to assessing the effectiveness of that drug and proposing alternative drug(s) or optimizing the drug if deemed appropriate. Such methods involve obtaining a sample containing a disease-causing pathogen from a patient, and then performing the steps described in any one or more of the embodiments of the invention described above.

It will be apparent to the skilled reader that while the invention has been described in the below examples with respect to viruses, particularly HIV, the present invention has broad applicability to any disease state where it is desired to correlate genotypic information with phenotypic profiles and assess the threshold at which a fold change resistance is clinically significant. One skilled in the art could readily take the following discussion of the invention with the HIV virus and through the exercise of routine skill apply this invention to other diseases (such as other viral infections, malignant cells, cancer, bacterial infections, other pathogens, and the like) to correlate genotypic information to predict phenotypic response, assess drug resistance, and eventually develop a treatment regime of drugs for a particular patient. One skilled in the art will also know that many virus species comprise many strains; for instance, HIV comprises HIV-2 in addition to HIV-1 and both groups are further divided into groups (such as groups O and M for HIV-1).

The above methods are diagnostic methods. Further aspects of the invention provide diagnostic kits for performing any one of the diagnostic methods of the invention described above. The invention further relates to a diagnostic system as herein described for use in any of the above described methods.

According to yet another embodiment, the present invention relates to a diagnostic system for predicting clinical response to a drug of a disease causing pathogen comprising: a) means for obtaining a genetic sequence of the disease producing pathogen; b) means for identifying at least one mutation in the genetic sequence of the disease producing pathogen; c) genotype database means comprising genotype entries; d) phenotype database means comprising phenotypes of patient fold change response values; e) clinical response database means comprising clinical response to drug treatment data for reference sample patients; f) correlation means correlating a genotype entry with a phenotype, where the genotype entry corresponds with the obtained genetic sequence of the disease producing pathogen; g) means for modeling clinical response to a drug of the disease causing pathogen by determining whether the patient fold change response is above a cut-off value, wherein the cut-off value is determined using the clinical response database means and comprises the fold change response value at which a clinically relevant diminished clinical response is observed; and h) means for predicting the clinical response to a drug of a disease by determining whether the patient fold change response is above the cut-off value.

As described above, the cut-off value is determined as a function of treatment response data in treated subjects, considering baseline pathogen load, baseline fold change resistance, baseline activity of co-administered drugs targeted to the pathogen, and treatment history. The means for predicting the resistance are preferably computer means.

A still further aspect of the invention relates to a computer apparatus or computer-based system adapted to perform any one of the methods of the invention described above.

In a preferred embodiment of the invention, said computer apparatus may comprise a processor means incorporating a memory means adapted for storing data; means for inputting data relating to the genotype exhibited by a particular disease causing pathogen; and computer software means stored in said computer memory that is adapted to perform a method according to any one of the embodiments of the invention described above and output a prediction of the resistance of a disease causing pathogen toward a drug.

A computer system of this aspect of the invention may comprise a central processing unit; an input device for inputting requests; an output device; a memory; and at least one bus connecting the central processing unit, the memory, the input device and the output device. The memory should store a module that is configured so that upon receiving a request to model the response to a drug of a disease causing pathogen, it performs the steps listed in any one of the methods of the invention described above.

In the apparatus and systems of these embodiments of the invention, data may be input by downloading the data from a local site such as a memory or disk drive, or alternatively from a remote site accessed over a network such as the internet. Data may be input by keyboard, if required.

The generated results may be output in any convenient format, for example, to a printer, a word processing program, a graphics viewing program or to a screen display device. Other convenient formats will be apparent to the skilled reader.

The means adapted to predict the resistance of a disease causing agent to a drug will preferably comprise computer software means. As the skilled reader will appreciate, once the novel and inventive teaching of the invention is appreciated, any number of different computer software means may be designed to implement this teaching.

According to a still further aspect of the invention, there is provided a computer program product for use in conjunction with a computer, said computer program comprising a computer readable storage medium and a computer program mechanism embedded therein, the computer program mechanism comprising a module that is configured so that upon receiving a request to predict the resistance of a disease to a drug, it performs the steps listed in any one of the methods of the invention described above.

The invention further relates to systems, computer program products, business methods, server side and client side systems and methods for generating, providing, and transmitting the results of the above methods.

The invention will now be described by way of example with particular reference to a specific system that implements the process of the invention. As the skilled reader will appreciate, variations from this specific illustrated embodiment are of course possible without departing from the scope of the invention.

EXAMPLE

Process Description of the Determination of Clinical Cut-Offs

Step 1: Clinical Data Base and Analysis Data Set

Figure 1A:
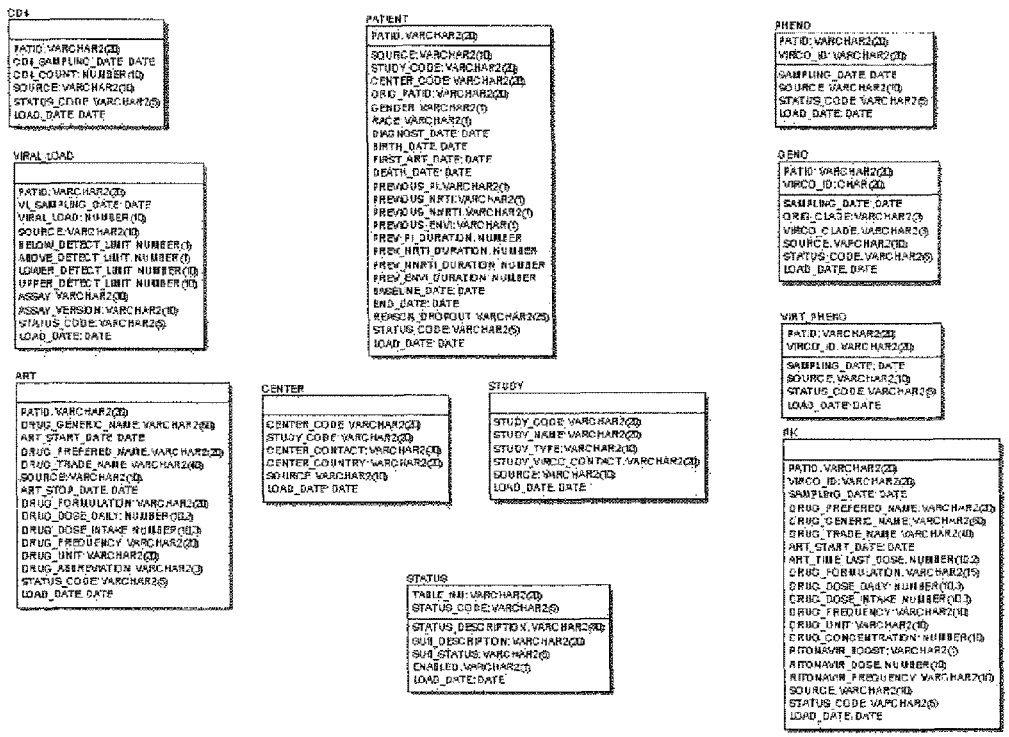
FIG. 1a: Example of the structure of a clinical data base used in the present invention.

Databases of studies for patients with tenofovir containing regimens and consisting of patient baseline demographic characteristics, clinical outcome results with viral load and resistance data (Fold change), were retrieved and remapped according to a common structure allowing a meta-analysis. The structure consisted of baseline sequence, viral load data set, viral load measurements and sampling dates (for example viral load within 3 months of starting new regimen and viral load assessment 8 and/or 24 weeks after beginning new regimen), CD4+ data set which contains CD4+ counts and sampling dates, resistance data set containing the fold changes to different antivirals and sampling dates; patient data set with patient information such as age, gender, race, treatment history; treatment data set with drug regimens, start and stop dates, doses, formulations, frequency of intake, regimen changes after resistance tests. The structure of such a clinical data base can be seen in FIG. 1a. The following table shows an example of characteristics of analysis datasets (8 week outcome) for individual drugs.

| | Range (Drug) |
|---|---|
| Median Baseline Viral Load (log) | 3.32 (TDF)-4.71 (boosted IDV) |
| Median background cPSS | 1.34 (ddC)-2.58 (LPV/r) |
| # regimens including the drug | 24 (unboosted APV)-1551 (3TC) |
| % from cohort data | 21% (unboosted APV)-83% (ddI-EC) |
| % with no resistance mutations | 14.5% (boosted APV)-75% (EFV) |

Figure 1B:
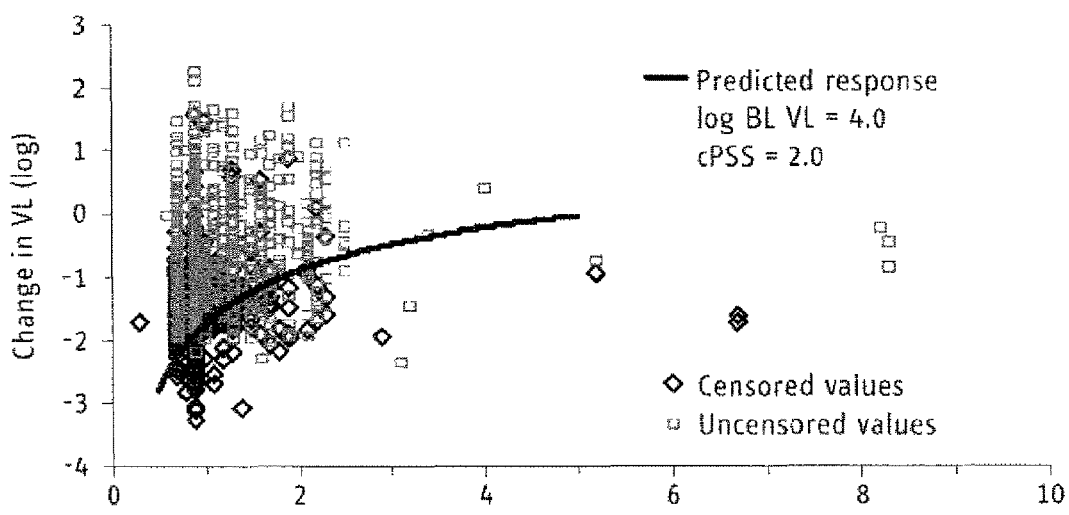
FIG. 1b: Example analysis dataset for d4T.

FIG. 1b shows an example analysis dataset for d4T. The viral load response data includes censored (<400 copies/ml) values. Parameters of the underlying uncensored distribution were estimated by maximum likelihood estimation in SAS (proc lifereg). The viral load response data are corrected for baseline viral load and cPSS.

Step 2: Modelling

The clinical outcome results (drop in viral load and response rate) were modelled as a function of baseline fold change (FC) as determined by virtual phenotype (see WO01/79540 and WO02/33402; also http://www.vircolab.com). The models applied were linear regression, logistic regression, and a classification tree. These models also took into account effects of the concomitant HIV drugs (PSS), baseline viral load (Baseline Log(V1)$_i$) and, optionally, treatment history in order to avoid bias introduced by imbalances of important characteristics. From the models, a prediction of clinical outcome could be made at different levels of the baseline fold change resistance.

Figure 2A:
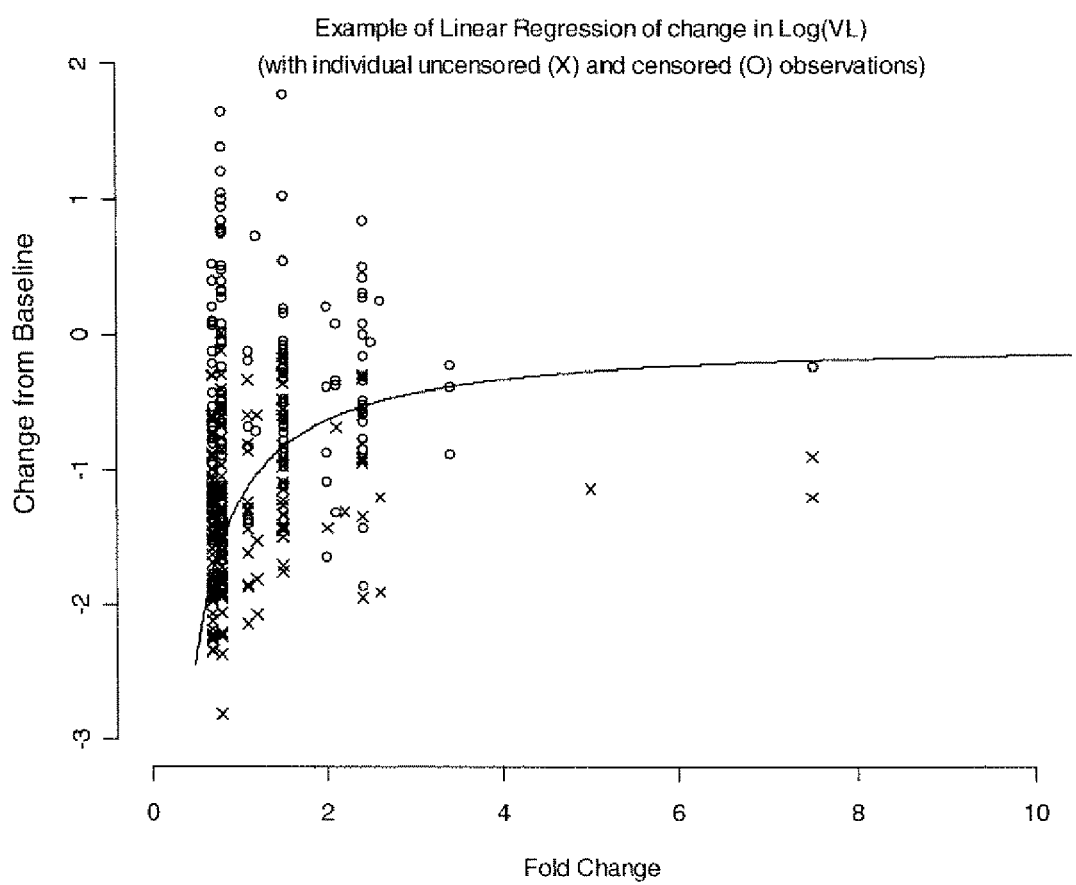
FIG. 2a: Example of linear regression curve showing censored and uncensored observations, where log viral load drop is modelled as a function of baseline fold change resistance.

In the linear regression model, the proposed equation was the following:

$$\text{LogVL drop}_i = \beta 0 + \beta 1 * \text{Baseline Log}(V1)_i + \beta 2 * \text{PSS}_i + \beta 3 * (1/\text{FC})_i + \xi_i$$

where i represented the patient, β0 the intercept, β1, β2 and β3 coefficients indicated the increase in log viral load drop per unit increase of respectively the baseline log VL, the number of sensitive drugs in the background regimen and the inverse of the baseline fold change. $\xi_i$ was a random error term indicating the deviation of the patient from the value predicted by the model. Interactions between all the factors were evaluated and other baseline characteristics, i.e treatment history, were added if relevant. After applying the regression model, the curve as depicted in FIG. 2a was obtained.

Figure 2B:
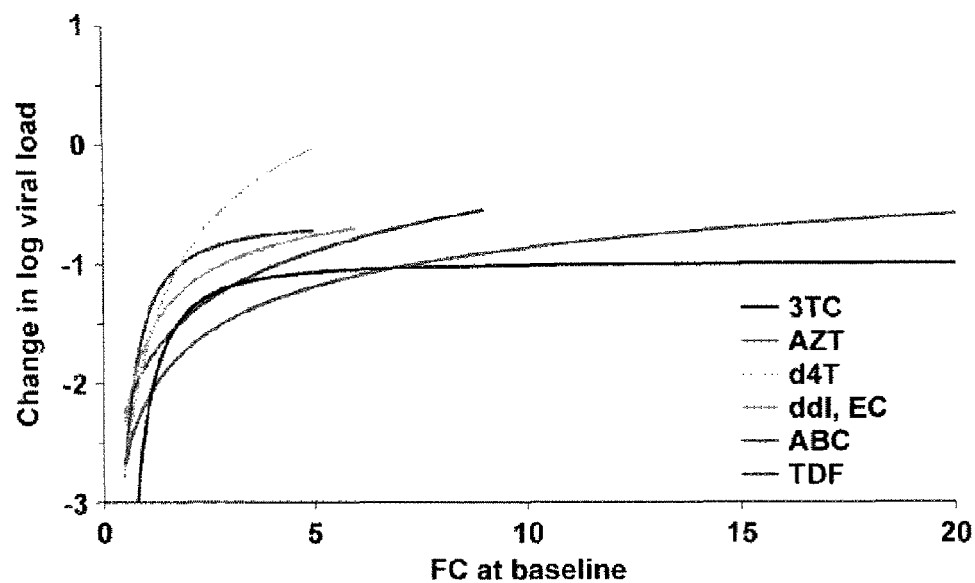
FIG. 2b: Example of linear regression curve of 8 week viral load response as a function of baseline phenotypic resistance for nucleoside(tide) RT inhibitors.
Figure 2C:
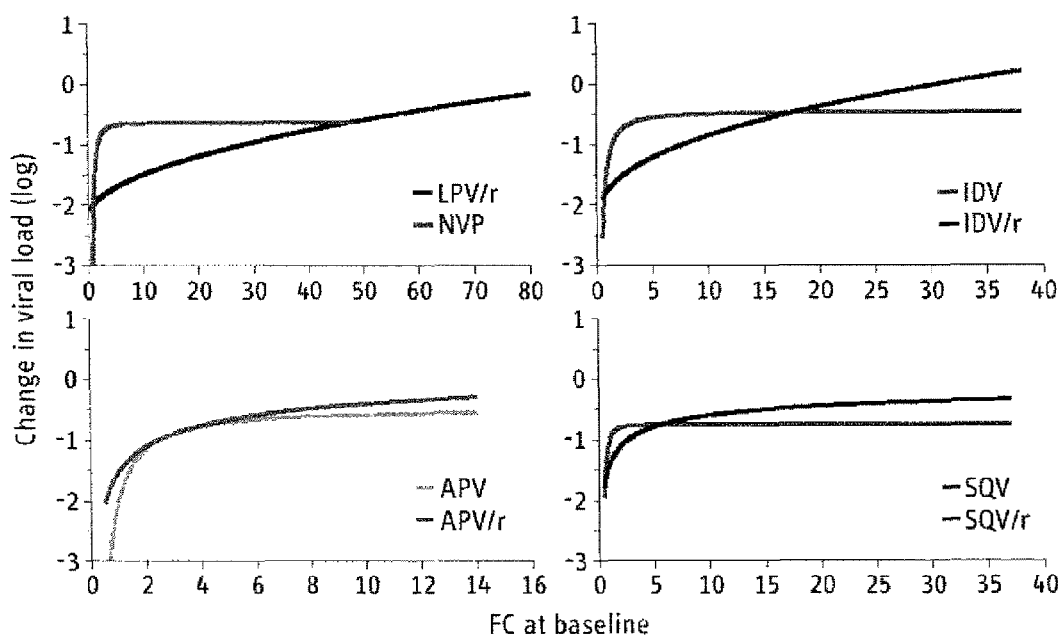
FIG. 2c: Example of linear regression curve of 8 week viral load response as a function of baseline phenotypic resistance for boosted and unboosted protease inhibitors.

Example curves showing linear regression models of 8 week viral load response as a function of baseline phenotypic resistance are shown in FIGS. 2b and 2c. The curves shown are for subjects with a log baseline viral load=4.0 and a cPSS score for the background regimen of 2.0. FIG. 2b shows models for nucleoside(tide) RT inhibitors (from top to bottom at FC=5, the respective curves represent d4T; TDF; ddI, EC; ABC; 3TC and AZT). FIG. 2c shows models for boosted and unboosted protease inhibitors (from top to bottom at FC=10 the respective curves represent: top left graph—NVP and LPV/r; top right graph—IDV and IDV/r; bottom right graph—SQV/r and SQV; bottom left graph—APV/r and APV).

Figure 2D:
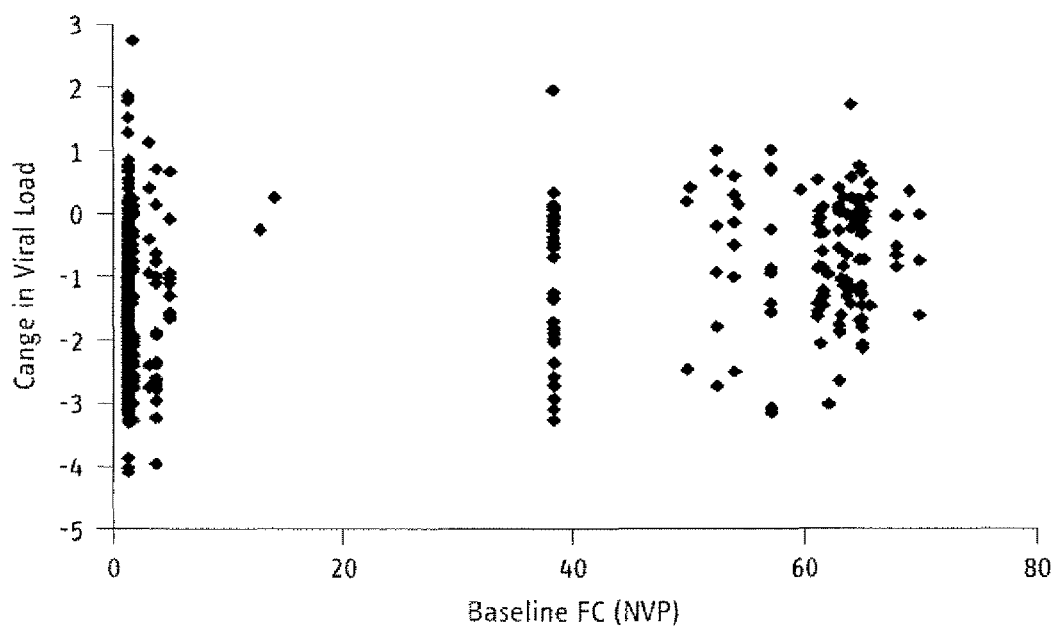
FIG. 2d: Example of change in viral load vs. baseline fold change for the NNRTI of neviripine (NVP).
Figure 2E:
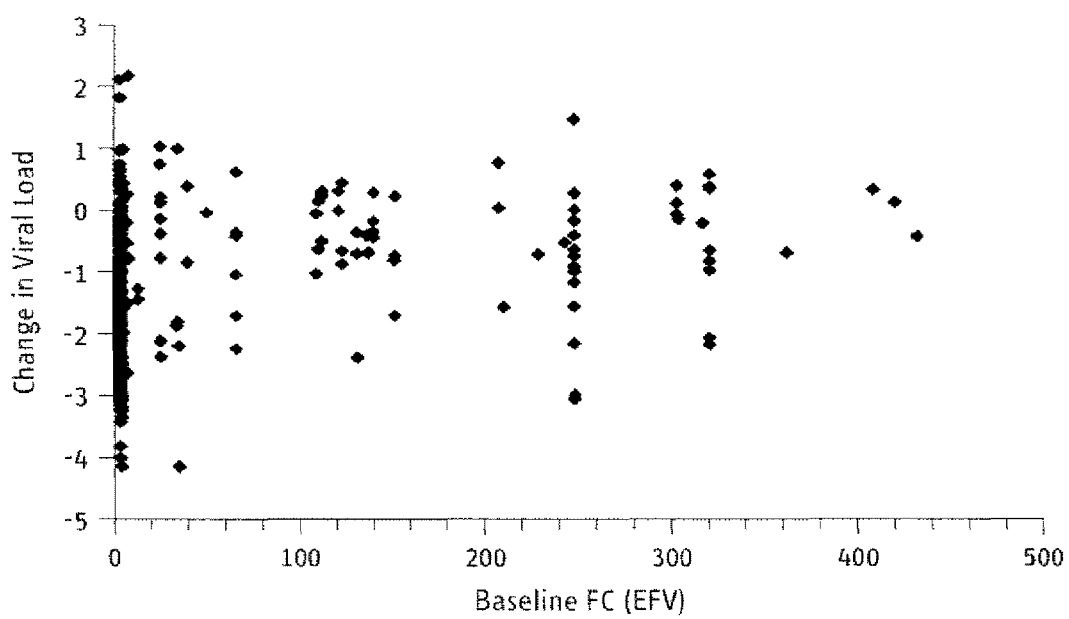
FIG. 2e: Example of change in viral load vs. baseline fold change for efavirenz (EFV).

A fundamental issue with modeling clinical outcome for non-nucleoside(tide) RT inhibitors is that the baseline fold change may have little effect on treatment response to current NNRTIs in NNRTI experienced patients. For the NNRTI of neviripine, polarisation of fold change values is observed (see FIG. 2d). Furthermore, an extremely broad dispersal of fold change values is observed for efavirenz (see FIG. 2e).

In a preferred embodiment of the linear regression model, more factors are included in order to obtain a more refined prediction of viral load response. These factors include for example a sensitivity score per drug class in addition to the overall sensitivity score of the background treatment (cPSS), previous exposure to the drug (naïve (Yes/No), naïve to PIs, naïve to NRTI's, etc. ... ). Furthermore, in the preferred embodiment, the fold change is transformed before inserting the figures in the model. The transformation to the fold change comprises a power-transformation ranging from $FC^{-3}$ to $FC^1$. In addition, a quadratic term in cPSS is preferably added.

Accordingly, a more general form of the equation given above may be expressed as:

$$\text{LogPLdrop}_i = \beta_0 + \beta_1 \text{Log}(\text{BaselinePL}_i) + \beta_2(\text{cPSS}_i) + \beta_3 (\text{cPSS}_i)^2 + \beta_4(\text{FC}_i)^P + \beta_5(H_5) + \ldots + \beta_n(H_n) + \epsilon_i$$

wherein p is a power transformation (e.g. ranging from −3 to 1) and $H_5$ to $H_n$ are treatment history parameters (e.g. naïve to antiretroviral therapy, naïve to NRTI treatment, etc. ... ) or parameters describing the background therapy as a function of a certain therapeutic class (e.g. the number of active NRTI's taken concomitantly with the drug under investigation).

Figure 2G:
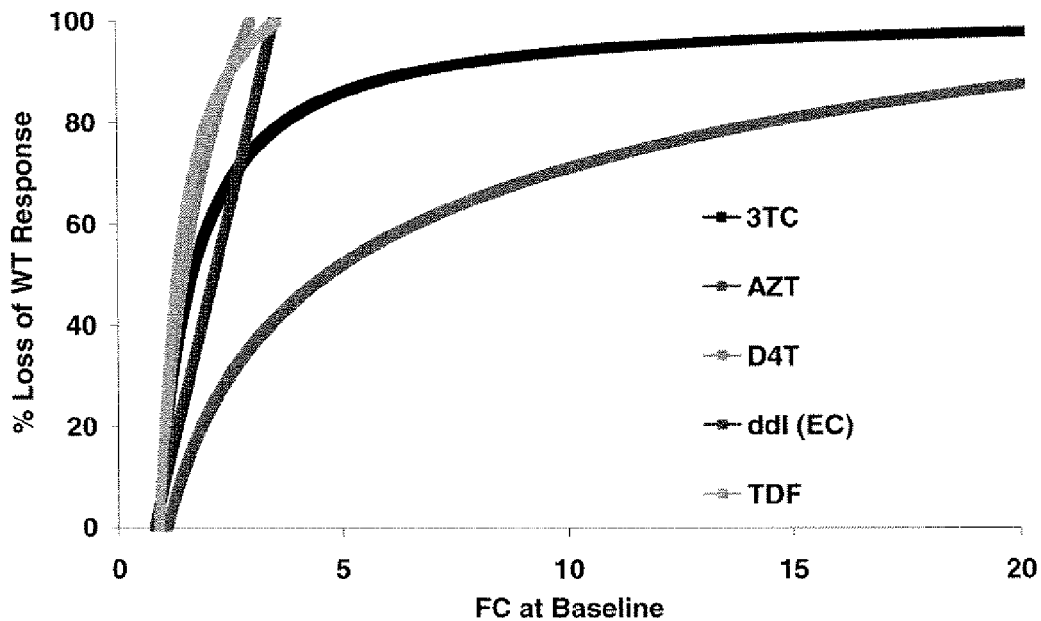
FIG. 2g: Drug Effect plotted as % response as a Function of Baseline Resistance for boosted and un-boosted Protease Inhibitors
Figure 2F:
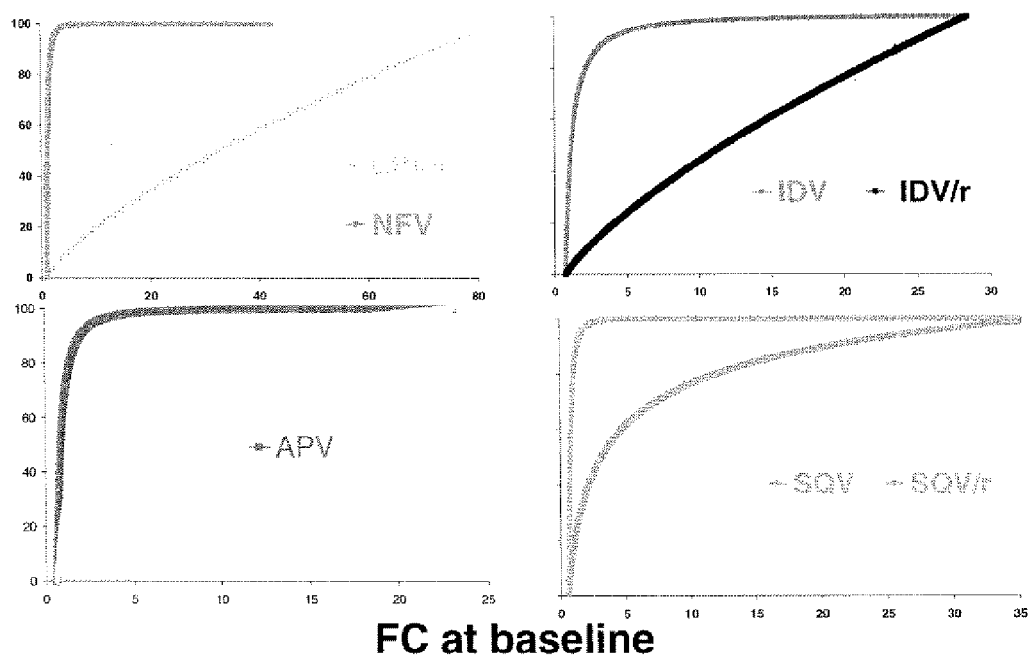
FIG. 2f: Drug Effect plotted as % response as a Function of Baseline Resistance for nucleoside(tide) inhibitors

Example curves showing linear regression models as calculated using this model are shown in FIGS. 2f and 2g. Here, the presentation of the data is different in that the % response is plotted, as calculated for the preferred CCO definition, rather than the viral load drop.

Figure 5A:
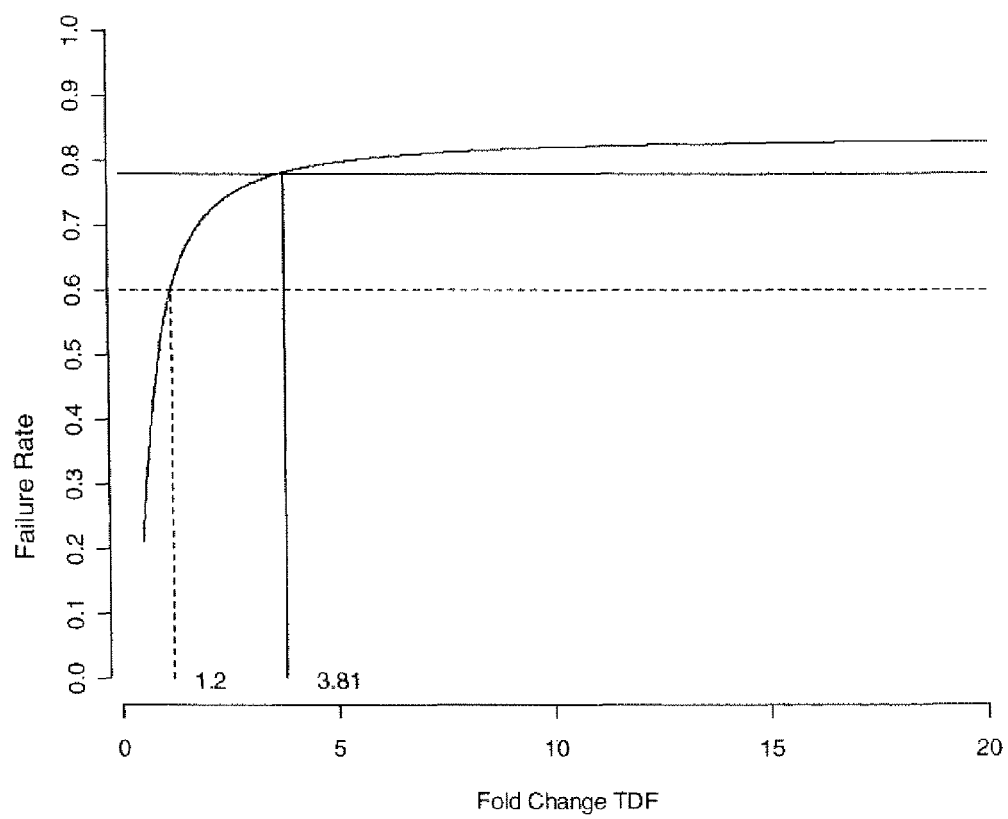
FIG. 5a: Example of logistic regression curve for TNF, where probability of failure is modelled as a function of baseline fold change resistance and a second definition of clinical cut-off is applied.
Figure 7:
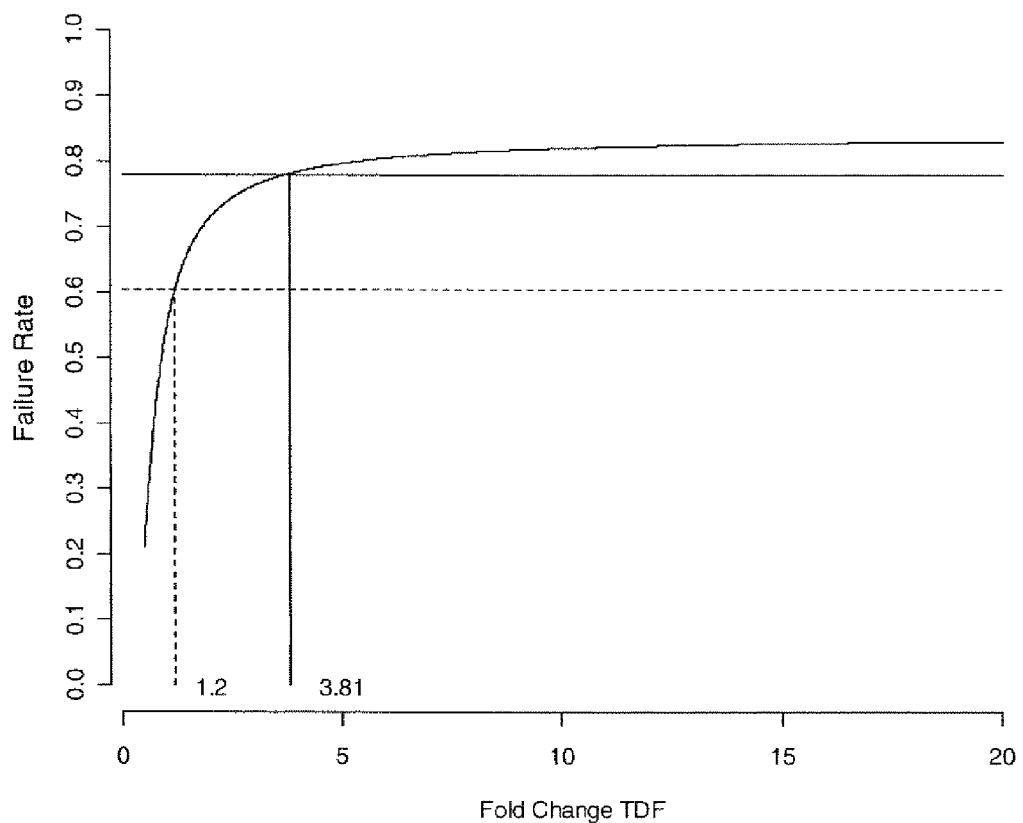
FIG. 7: Example of logistic regression curve for TNF, where probability of failure is modelled as a function of baseline fold change resistance and a third definition of clinical cut-off is applied.

In the logistic regression, the proposed equation was the following:

$$Prob \text{ of success} = \frac{\exp\left(\begin{array}{l}\beta_0 + \beta_1 \text{Log}(BaselineVL_i) + \\ \beta_2(PSS_i) + \beta_3(1/FC_i)\end{array}\right)}{1 + \exp\left(\left(\begin{array}{l}\beta_0 + \beta_1 \text{Log}(BaselineVL_i) + \\ \beta_2(PSS_i) + \beta_3(1/FC_i)\end{array}\right)\right)}.$$

where β1, β3, and β3 represented the log odds ratio of success for the corresponding factors in the model. After applying the logistic regression model, the curves as depicted in FIGS. 5a and 7 were obtained. In the classification trees model, tree-structured rules were constructed in order to classify patients in successes (undetectable viral load after treatment) and failures. The same parameters as for the other techniques were considered. The tree shown in FIG. 8 was obtained after applying the classification tree model.

When viral load results under the detection limits are obtained, biases could be introduced if the detection limit values are considered when calculating viral load drops and using those in the linear regression model. To avoid this, censoring needed to be taken into account and therefore the PROC LIFEREG facility in the SAS package was employed.

An advantage of this regression model is that it takes into account the maximum amount of information present in the data, i.e. correlating specific clinical responses with specific Fold changes while the other two models clusters the patients in two groups (successes versus failures), thus not taking into account differences in responses within the same group. Estimates are corrected for covariates in the model (e.g. background regimen) and therefore, they do not suffer from imbalances in the covariates. Conclusions are limited to patients with covariates that are represented in the clinical database.

Logistic regression does not suffer from the censoring problem and the probability of success is an intuitive way of interpreting clinical outcome. However, by binning the viral load into successes and failures, part of the information of the continuous variable viral load is lost. Estimates are also corrected for covariates as for linear regression.

Figure 8A:
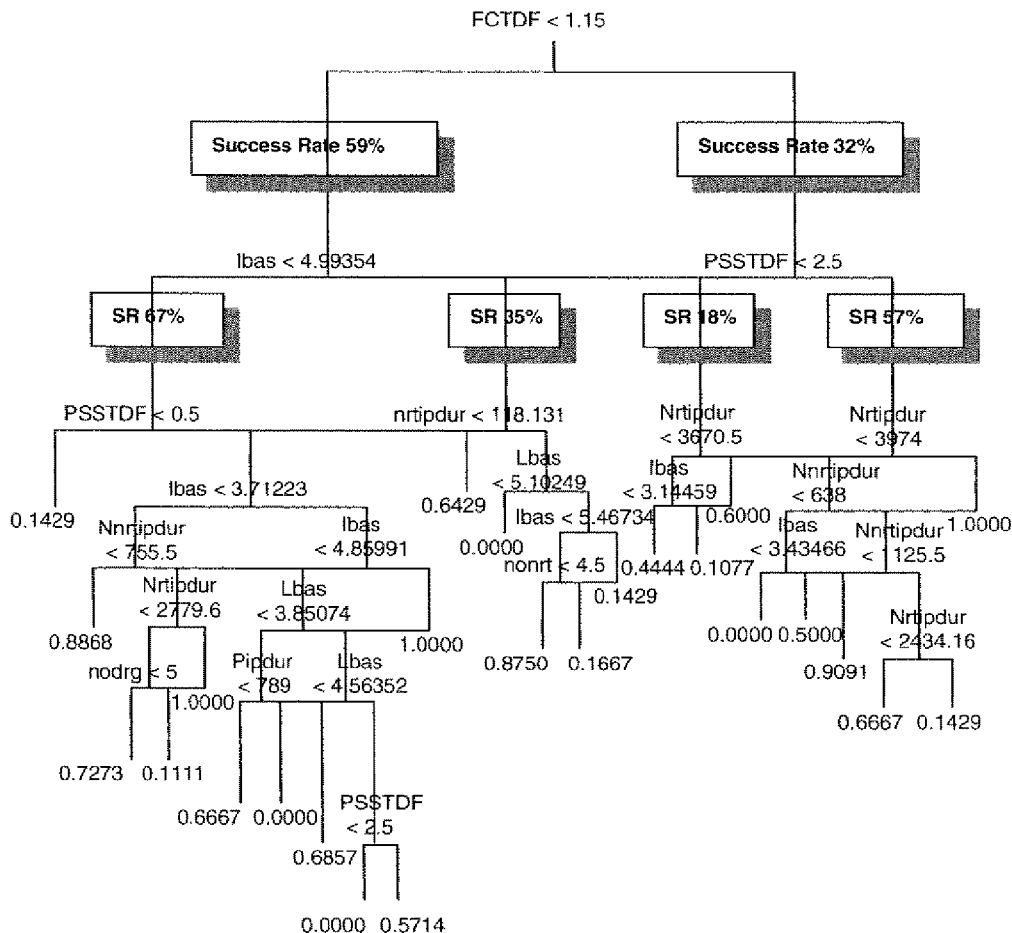
FIG. 8a: Example of classification tree for TNF. This gives results of the same order as the linear and logistic regression methodologies.
Figure 8B:
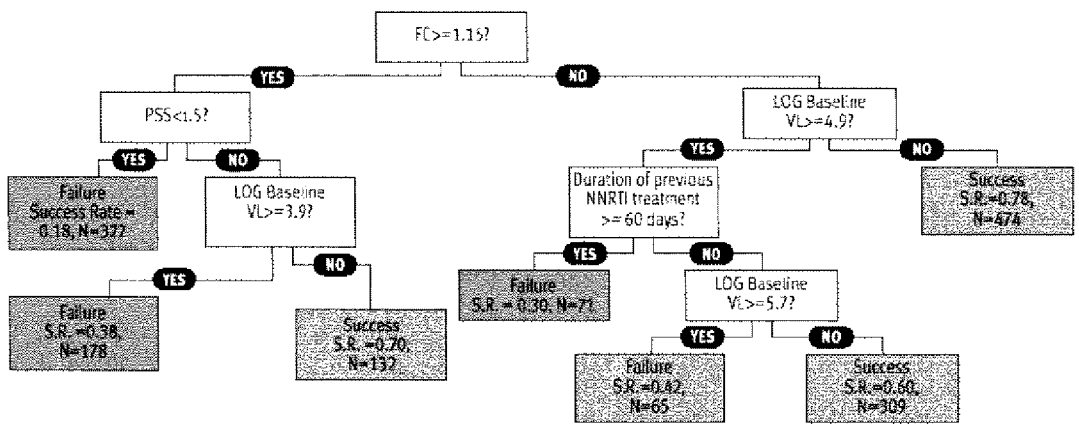
FIG. 8b: Example of classification tree for 3TC.
Figure 8C:
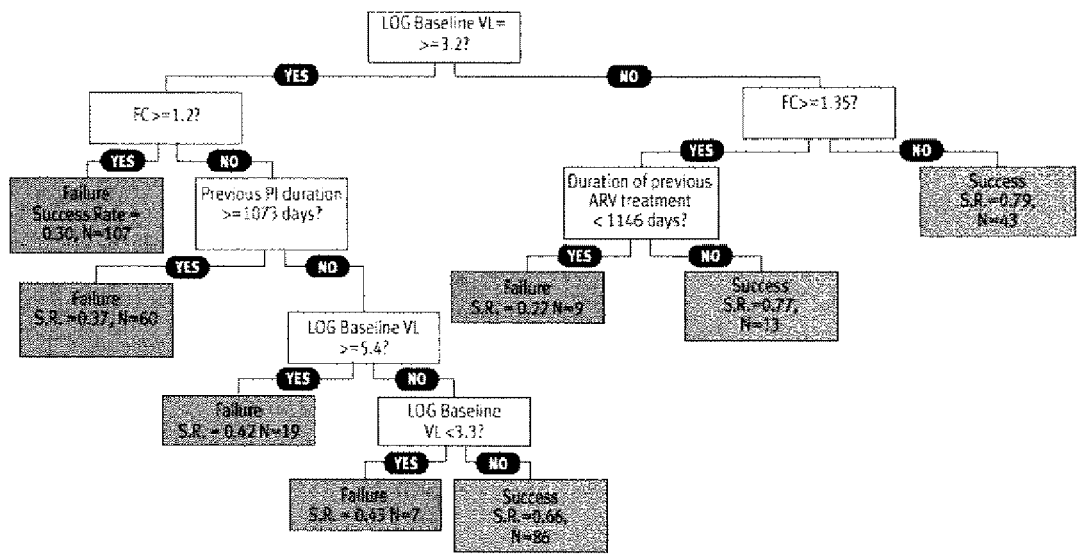
FIG. 8c: Example of classification tree for TDF assuming that the cost of classifying a failed regimen as a success is 1.5 times the cost of classifying a successful regimen as a failure.

Classification trees are very visual and easy to interpret, but they have the disadvantage that the decisions do not take into account the value of other relevant parameters. This implies that imbalances for other parameters may influence the decision taken for a certain parameter. However, they provide insights in the importance of several parameters and this can be helpful in the fitting process of the other approaches. FIGS. 8a, 8b and 8c show examples of classification trees. FIG. 8b shows a classification tree for 3TC, whilst FIG. 8c shows a classification tree for TDF assuming that the cost of classifying a failed regimen as a success is 1.5 times the cost of classifying a successful regimen as a failure.

Step 3: Determination of the Clinical Cut-Off.

Clinical responses were predicted in the models developed in previous step 2. The approach is to identify two cutoffs per drug: a "lower" cutoff which represents the fold change at which the response begins to be lost, and an "upper" cutoff which represents the fold change at which the response is essentially gone. In order to determine the fold changes at which clinically relevant diminished clinical responses can be observed, three definitions of clinical cut-offs were considered:

Definition 1

Sensitive: predicted viral load drop is more than 0.6 logs.
Intermediate resistant: predicted viral load drop is between 0.2 and 0.6 logs.
Resistant: predicted viral load drop is less than 0.2 logs.

The lower and higher cutoffs are defined as the fold change with expected log viral load drops of $\geq 0.6$ and $\leq 0.2$ respectively.

This definition of clinical cut-off addresses the potency of an entire combination regimen and is highly dependent on the characteristics of the specific patient regimens analysed.

Definition 2

The maximum effect was defined as the treatment effect at fold change 1, and the minimum effect was defined as the treatment effect at a very high fold change (i.e. when the curve reached a plateau). The effect range was then the difference between the maximum effect and the minimum effect.

Sensitive: the predicted treatment effect is more than 80% of the effect range.
Intermediate resistant: the predicted treatment effect is between 20% and 80% of the effect range.
Resistant: the predicted treatment effect is less than 20% of the effect range.

The lower and higher cutoffs are defined as the fold change associated with an expected 20% and 80% decrease respectively of the reference activity of the drug within the regimen.

Cutoffs obtained using definition 2 do not address the potency of the entire treatment regimen, but rather give an estimation of the activity of the drug within the regimen. The absolute magnitude of the viral load drop depends on specific covariates.

Definition 3

Definition 3 was a variant of definition 2. The lower cut-off was defined as the fold change that most optimally distinguished patients between successful and unsuccessful treatments.

Using definition 3, breakpoints determined by classification trees are applicable only to a subset of patients unless fold change is selected at the first tree node. Classification trees are easy to interpret but the cutoffs do not indicate the magnitude of the viral load reduction expected for the whole regimen or the drug within the regimen. Breakpoints determined by the linear and the logistic regression models are close to the lower cutoffs as defined by definition 2, except for the boosted protease inhibitors.

The methodology was applied for Tenofovir on a population taking two active drugs besides tenofovir and with a baseline Log(V1) of 4.

Figure 3A:
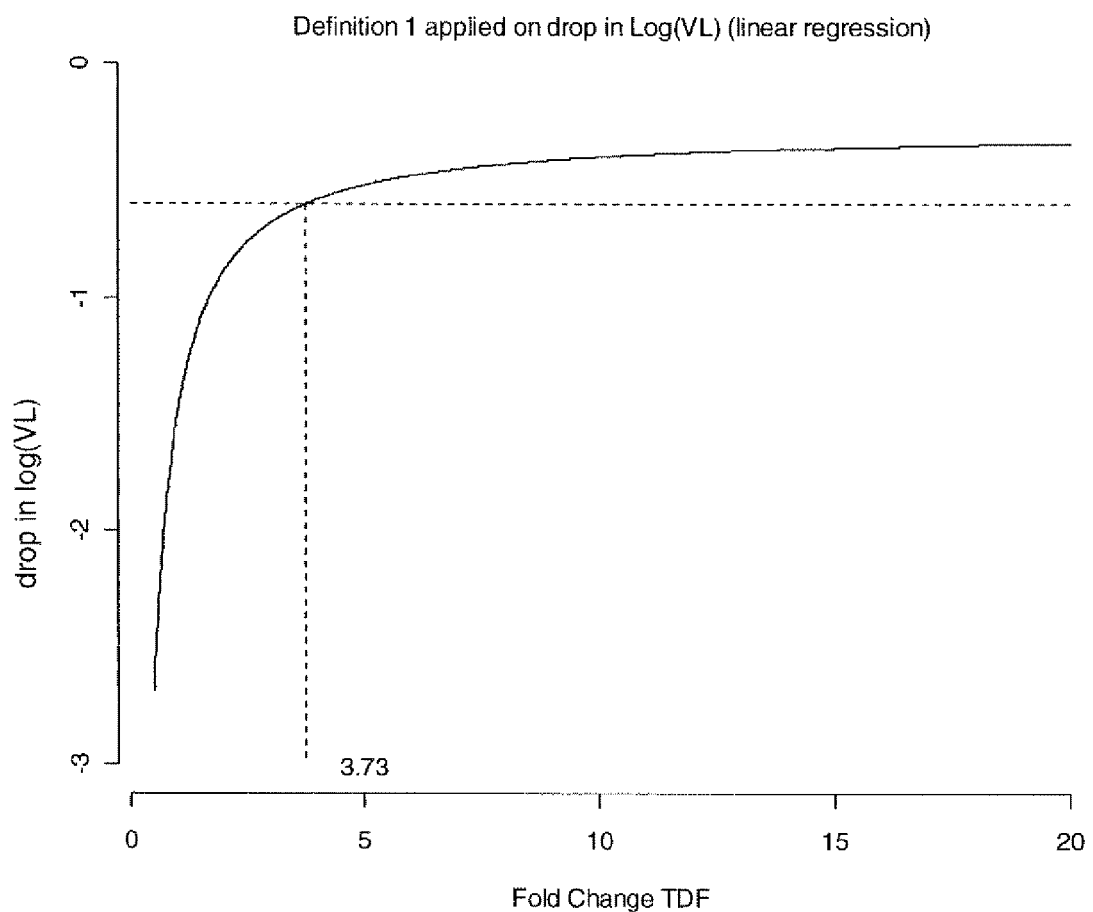
FIG. 3a: Example of linear regression curve for TNF, where log viral load drop is modelled as a function of baseline fold change resistance and a first definition of clinical cut-off is applied.

When we applied definition 1 on the linear regression model, the observed drop in log viral load was −0.6 at fold change 3.73 (FIG. 3a). No higher cut-off could be derived as this population experienced a drop in Log(VL) greater then 0.2 even with a high baseline fold change for tenofovir. This could be explained by the effect of the active background regimen in this population.

Figure 4A:
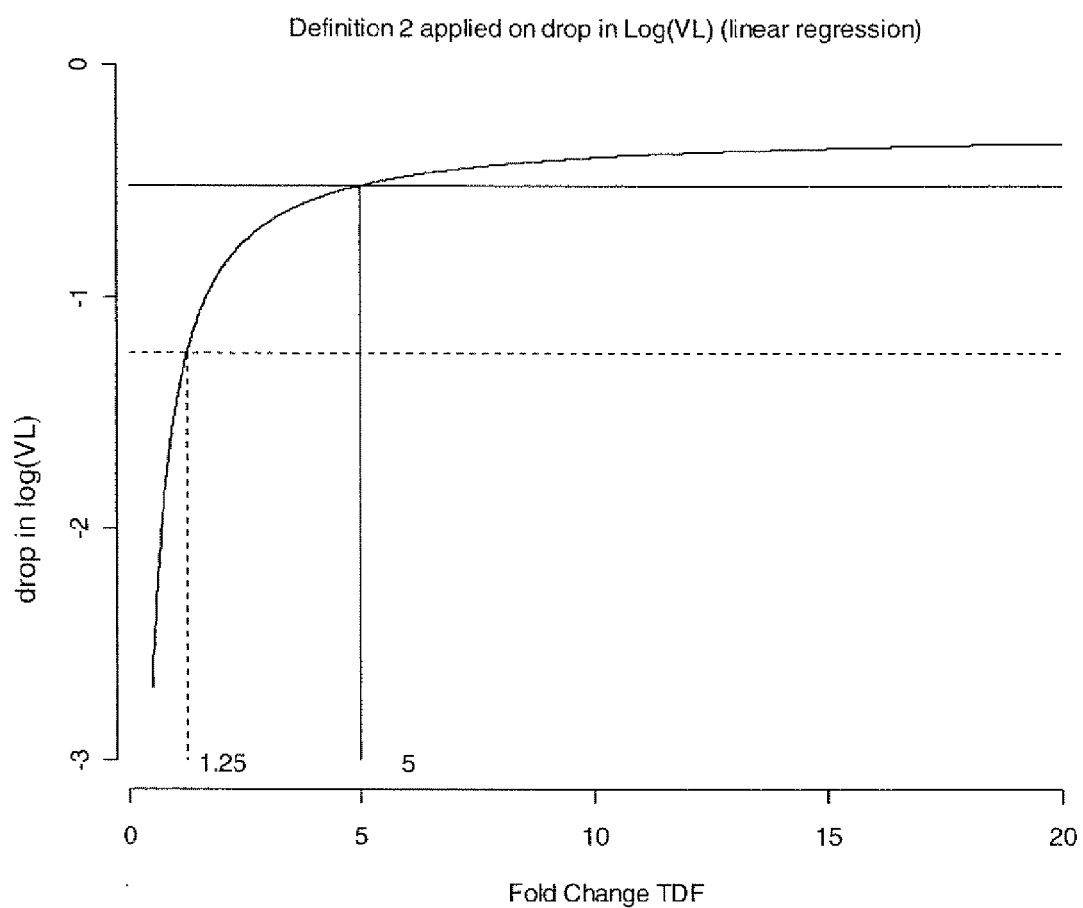
FIG. 4a: Example of linear regression curve for TDF, where log viral load drop is modelled as a function of baseline fold change resistance and a second definition of clinical cut-off is applied.

When we applied definition 2 on the linear regression model (FIG. 4a), the observed drop in log viral load was −1.48 at fold change 1, and −0.28 at the assymptotic fold change. Therefore the effect range was −0.28+1.48=1.2.

20% of this effect range was observed at fold change 5 (and this value was considered as the upper clinical cut-off value).

80% of the effect range was observed at fold change 1.25 (and this value was considered as the lower clinical cut-off value).

To predict the resistance according to this regression model, we determined whether the patient fold change resistance was above, below, or in between the clinical cut-off as calculated according to definition 2. So, when the FC of patient was of 0.8 (below the lower clinical cut-off), a normal clinical response was predicted. If the FC of the patient was of 2 (above the lower clinical cut-off and below the upper clinical cut-off), a reduced clinical response was predicted. If the FC was of 7 (above the clinical cut-off), then the clinical response was predicted as being minimal.

Figure 6:
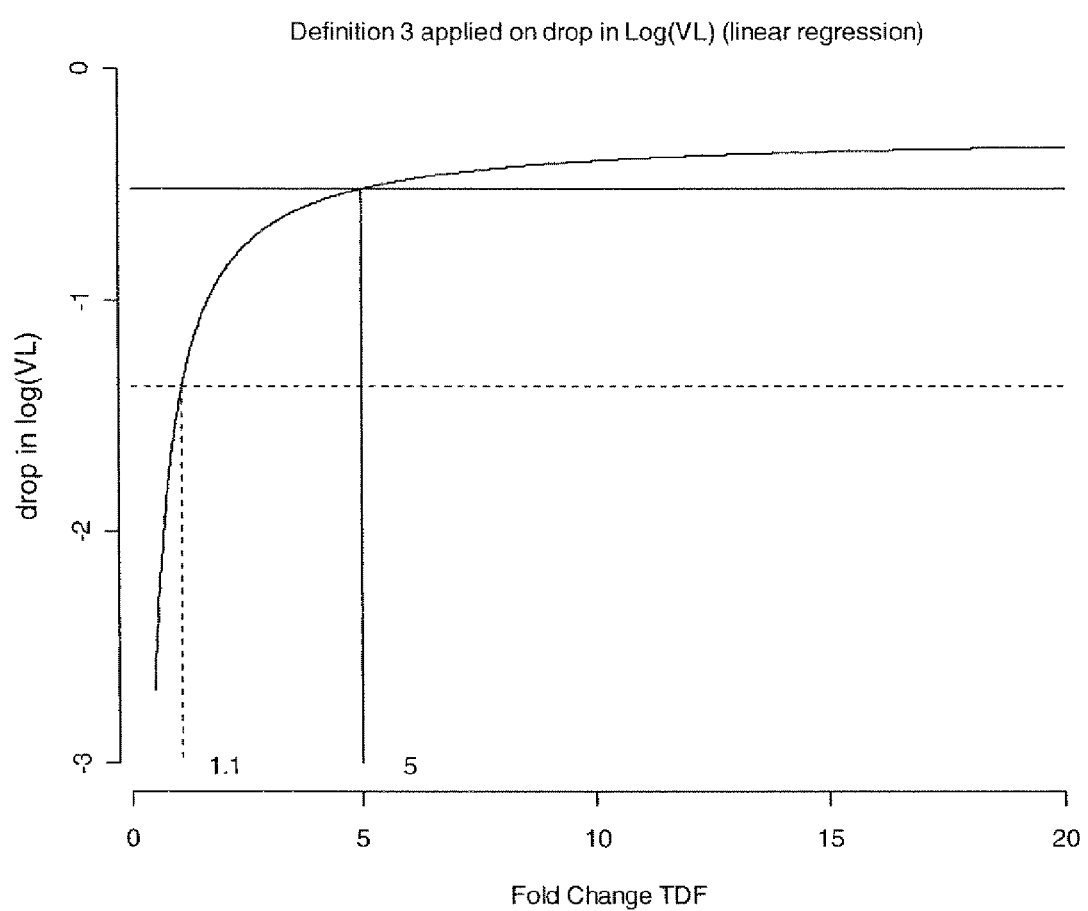
FIG. 6: Example of linear regression curve for TNF, where log viral load drop is modelled as a function of baseline fold change resistance and a third definition of clinical cut-off is applied.

Definition 2 was also applied to the logistic model (FIG. 5a) and this resulted in a lower cut-off at 1.2 FC and a higher cut-off at 3.81 FC. The results for definition 3 are depicted in FIGS. 6 and 7.

The Tenofovir results for the population with 2 active drugs in the regimen and a baseline Log(VL) of 4 are summarized in the Table below.

From the Table, it can be derived that the lower cut-off for definition is 1.2 and the higher cut-off ranges from 3.81 to 5 for the population of patients taking 2 active drugs besides tenofovir and with a baseline log(VL) of 4. The variation in cut-offs determined by the different definitions is a result of the different influence of the covariates such as PSS and log VL. That is, the influence of the covariates is significant when using definition 1 and less significant when using definition 2.

Definition 1 can only be applied on the linear regression model. The clinical cut-offs determined using definition 1 are highly dependent on the characteristics of the subpopulation. This is due to the fact that definition 1 describes the potency of the whole drug regimen while definition 2 is related only to the activity of the drug under consideration and its resistance profile. In other words, the activity of the background regimen together with the drug under investigation determines the viral load drop that the patient will experience and hence the dependence of the cut-off on the background regimen. The activity of the background regimen does not change the resistance profile in a profound way, therefore the clinical cut-offs do not vary considerably with the population characteristics.

| Definition of Clinical cut-off | Population | Properties of the subgroup | Linear Regression | | Logistic Regression | | Classification Tree | |
|---|---|---|---|---|---|---|---|---|
| | | | Lower CO | Higher CO | Lower CO | Higher CO | Lower CO | Higher CO |
| Definition 1 | Subgroup 1 | PSS = 2, baseline Log (VL) = 4 | 3.73 | >assay limit | NA | NA | NA | NA |
| | Subgroup 2 | PSS = 0, baseline Log (VL) = 4 | 1.68 | 3.8 | NA | NA | NA | NA |
| | Subgroup 3 | PSS = 2, baseline Log (VL) = 5 | >assay limit | >assay limit | NA | NA | NA | NA |
| | Overall | | NA | NA | NA | NA | NA | NA |
| Definition 2 | Subgroup 1 | PSS = 2, baseline Log (VL) = 4 | 1.25 | 5 | 1.2 | 3.81 | NA | NA |
| | Subgroup 2 | PSS = 0, baseline Log (VL) = 4 | 1.25 | 5 | 1.16 | 3.36 | NA | NA |
| | Subgroup 3 | PSS = 2, baseline Log (VL) = 5 | 1.25 | 5 | 1.17 | 3.4 | NA | NA |
| | Overall | | 1.25 | 5 | NA | NA | NA | NA |
| Definition 3 | Subgroup 1 | PSS = 2, baseline Log (VL) = 4 | 1.1 | 5 | 1.2 | 3.81 | 1.15 | NA |
| | Subgroup 2 | PSS = 0, baseline Log (VL) = 4 | 1.1 | 5 | 1.2 | 3.36 | 1.15 | NA |
| | Subgroup 3 | PSS = 2, baseline Log (VL) = 5 | 1.1 | 5 | 1.2 | 3.4 | 1.15 | NA |
| | Overall | | 1.1 | 5 | 1.2 | NA | 1.15 | NA |

NA: Not Applicable

Figure 3B:
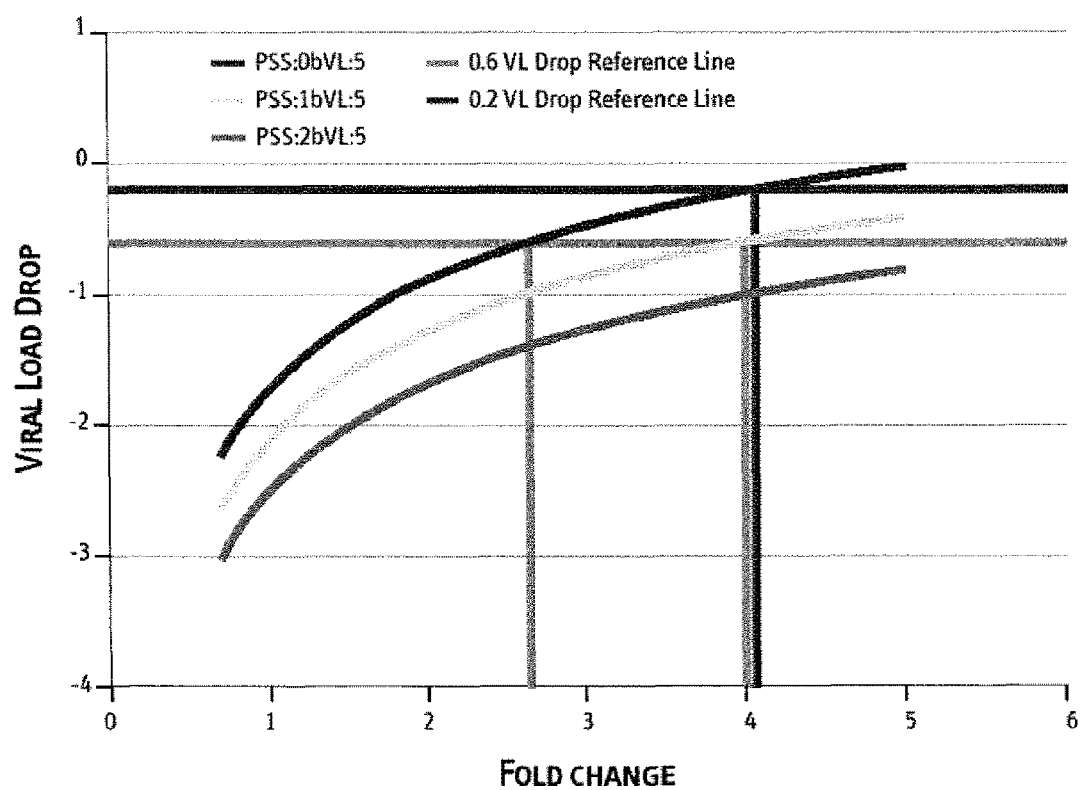
FIG. 3b: Example of linear regression curve for d4T, where viral load drop is modelled as a function of fold change and a second definition of clinical cut-off is applied.

Both linear and logistic regression models give similar results for definition 2. When we applied definition 1 on the linear regression model for patients with a log baseline viral load of 5 and all patients taking two active drugs in addition to d4T(stavudine), a viral load drop of more than 0.6 log copies/mL for any fold change of d4T is predicted (FIG. 3b). The viral load drop is predicted to be −0.6 logs and −0.2 logs at fold changes 2.6 and 4.0 for patients with a log baseline viral load of 5 and taking no active drugs in addition to d4T (see FIG. 3b).

Figure 4B:
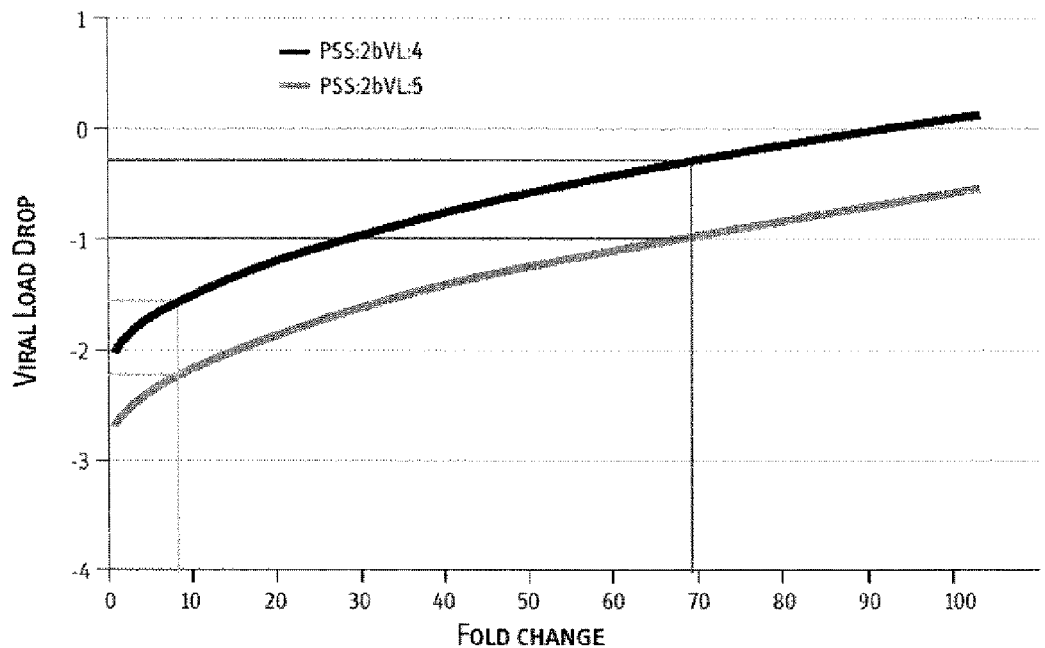
FIG. 4b: Example of lower and upper cutoffs determined using definition 2 for lopinavir/r if viral load is modeled using linear regression.
Figure 5B:
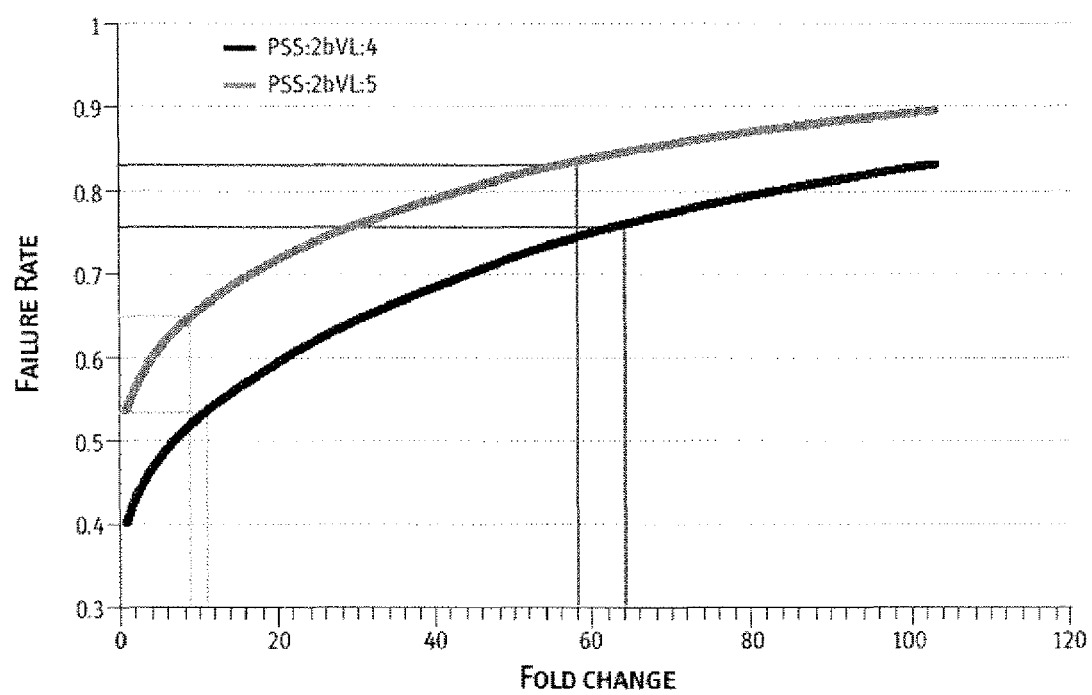
FIG. 5b: Example of lower and upper cutoffs determined using definition 2 for lopinavir/r if the failure rate is modelled using logistic regression.

Lower and upper cutoffs determined using definition 2 for lopinavir/r are shown in FIG. 4b as 8 and 69 respectively for the whole population if viral load is modeled using linear regression, while the lower and upper cutoffs are 11 and 64, 10 and 60, and 9 and 58 respectively for populations with log baseline VL/background PSS of 4/2, 5/0 and 5/2 respectively if the failure rate is modeled using logistic regression (see FIG. 5b). The PSS is not statistically significant in this example.

Figure 4C:
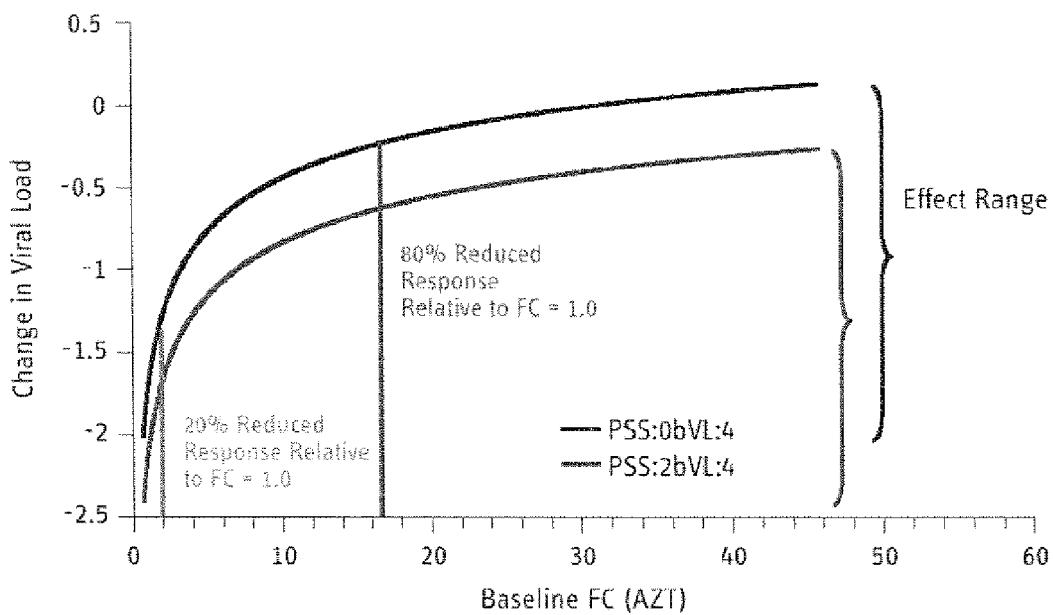
FIG. 4c: Example of lower and upper cutoffs determined using definition 2 for AZT if viral load is modelled using linear regression. Curve shows the change in viral load vs. the fold change.
Figure 4D:
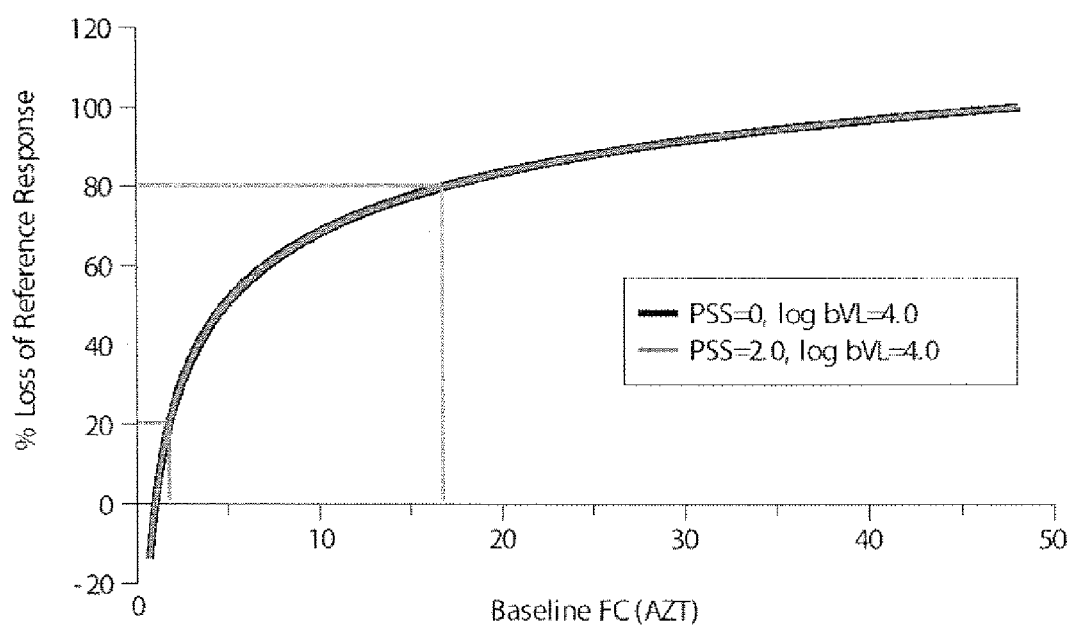
FIG. 4d: Example of lower and upper cutoffs determined using definition 2 for AZT if viral load is modelled using linear regression. Curve shows the % loss of reference response vs. the fold change.

Lower and upper cutoffs determined using definition 2 for boosted saquinavir for the logistic model were 1.7 and 13.2, and 1.7 and 12.9 respectively for populations with log baseline viral load/phenotypic sensitivity score for the background regimen of 4/2 and 5/0 respectively. Lower and upper cutoffs by linear regression for saquiavir/r were 1.6 and 12.3 respectively for the whole population Lower and upper cutoffs determined using definition 2 for AZT are shown in FIGS. 4c and 4d if viral load is modeled using linear regression. FIG. 4c shows the change in viral load vs. the fold change whilst FIG. 4d shows the % loss of reference response vs. the fold change.

Further tests with records for >13,000 patients yielded ~3150 regimens with the required baseline and outcome variables, ranging from 60 regimens including boosted SQV soft gel to 1546 including 3TC. Median log baseline viral load ranged from 3.8 (regimens with tenofovir) to 4.7 (regimens with boosed indinavir). Median PSS of background regimens was 2 (range 0-7). The following table shows results of preliminary VirtualPhenotype™ Clinical Cutoffs for nucleosides(tides) and boosted and unboosted protease inhibitors from a preliminary linear regression analysis. The fold change values associated with a 20% diminution of virologic response at 8 weeks and an 80% diminution of virologic response compared to the maximal response are shown with a 95% confidence interval in square brackets.

| DRUG | VIRTUALPHENOTYPE ™ PREDICTED FC OF WILD TYPE CLINICAL ISOLATES | VIROLOGIC RESPONSE | |
|---|---|---|---|
| | | 20% REDUCTION | 80% REDUCTION |
| AZT zidovudine | 0.8 | 1.8 [1.5-2.5] | 17 [10-25] |
| 3TC lamivudine | 0.8 | 1.1 [1.1-1.2] | 2.6 [1.9-4.6] |
| D4T stavudine | 0.7 | 1.3 [1.2-1.4] | 3.4 [3.1-3.6] |
| ddI didanosine (extended release) | 0.6 | 1.3 [1.2-1.9] | 3.6 [2.8-4.9] |
| ABC abacavir | 0.6 | 1.6 [1.1-2.6] | 5.8 [1.7-7.4] |
| TDF tenofovir | 0.8 | 1.2 [1.1-1.5] | 2.5 [1.7-3.8] |
| IDV indinavir | 0.7 | 1.2 [1.1-1.9] | 3.4 [1.9-16.4] |
| IVD/r Indinavir/r | | 3.5 [1.1-8.4] | 25 [1.8-31] |
| NFV nelfinavir | 0.9 | 1.1 [1.1-1.3] | 2.2 [1.7-5.3] |

-continued

| DRUG | VIRTUALPHENOTYPE ™ PREDICTED FC OF WILD TYPE CLINICAL ISOLATES | VIROLOGIC RESPONSE | |
|---|---|---|---|
| | | 20% REDUCTION | 80% REDUCTION |
| SQV | 0.6 | 1.1 | 2.0 |
| saquinavir | | [1.1-2.1] | [1.7-18] |
| SQV/r | | 1.6 | 12 |
| Saquinavir/r | | [1.3-4.8] | [5.8-27] |
| AMP | 0.6 | 1.2 | 3.4 |
| amprenavir | | [1.1-2.4] | [1.7-10.2] |
| AMP/r | | 1.5 | 6.8 |
| amprenavir/r | | [1.2-2.6] | [3.6-10.5] |
| LPV/r | 0.8 | 6.9 | 56 |
| Lopinavir/r | | [2.1-17.4] | [29-67] |

Similar values were determined in logistic regression models. While the magnitude of the virologic response for individual patients is affected by covariates such as viral load and PSS, FC values associated with fractions of the effect range are not.

Further test results showed that the clinical cutoffs for 20% reduced response after 8 weeks were low (1.1 to 1.2 for unboosted PIs), but higher than Virco type predicted fold changes for wild type clinical isolates (0.73 (ABC) to 1.07 (AZT) for NRTIs, 0.63 (APV) to 0.87 (NFV) for PIs). Clinical cutoffs for 80% reduced response were 3.4 (APV, IDV) for unboosted PIs. Clinical cutoffs for boosted PIs were higher: 1.5 (APV/r) for 20% reduction and 6.8 (APV/r) for 80% reduction. Among the treatment regimens analysed, sensitivity classes defined by these clinical cutoffs showed different rates of virologic response (viral load drop of more than 1.0 log for BQL at 8 weeks) to regimens including the drug: 70 to 92% for fold changes less than the lower clinical cutoff, 39 to 68% for fold changes between the upper and lower clinical cutoffs, and 18 to 50% for fold changes above the upper clinical cutoff.

In another example the following linear regression model is used for d4T with clinical cutoff definition 2 when Log(BaselineVL)=4, lower reference fold change=0.9 and upper reference fold change=3, cPSS=2, PSS[NRTI]=1 and NRTI [naïve]=0, using the following linear regression:

$$VLdrop = 2.91 - 0.63 \text{Log}(BaselineVL) - 1.66(FC^{0.6}) - 0.99(cPSS) + 0.15(cPSS^2) - 0.18(PSS[NRTI]) + 0.91(NRTI[naïve]).$$

The NRTI[naïve] value represents whether the patient is naïve to nucleoside RT inhibitors. If yes, value=1, if no, value=0. The PSS[NRTI} represents the phenotypic sensitivity score for NRTIs, i.e the number of active NRTIs in the background regimen for the patient.

Stage 1: Calculate VL drop at the lower reference FC (drug is fully active) and the VL drop at the upper reference FC (minimal activity of the drug). This leads to a lower VL drop of −2.94 and an upper VL drop of −2.03.

Stage 2: Calculate VL drop when drug has lost 20% of its activity and the VL drop when drug has lost 80% of its activity. This gives values of VL drop=−2.76 for 20% and −2.21 for 80% loss of activity.

Stage 3: Determine Fold change equivalent to VL drop at 20% and 80% loss of activity by inserting values for VL drop into the above equation and calculating FC. This gives FC values of 1.08 and 2.18. Consequently, the lower and upper clinical cutoff values for d4T are modeled as 1.1 and 2.2 respectively.

Step 4: Validation of the Cut-Offs

The models were validated using bootstrapping and repeating the steps described above several times. Bootstrapping is a resampling technique in which pseudo-populations of the same size as the original population are created by randomly drawing samples from the original population. Analysis of each of these populations gives a sense of the sampling variability of the clinical cut-off.

Figure 9:
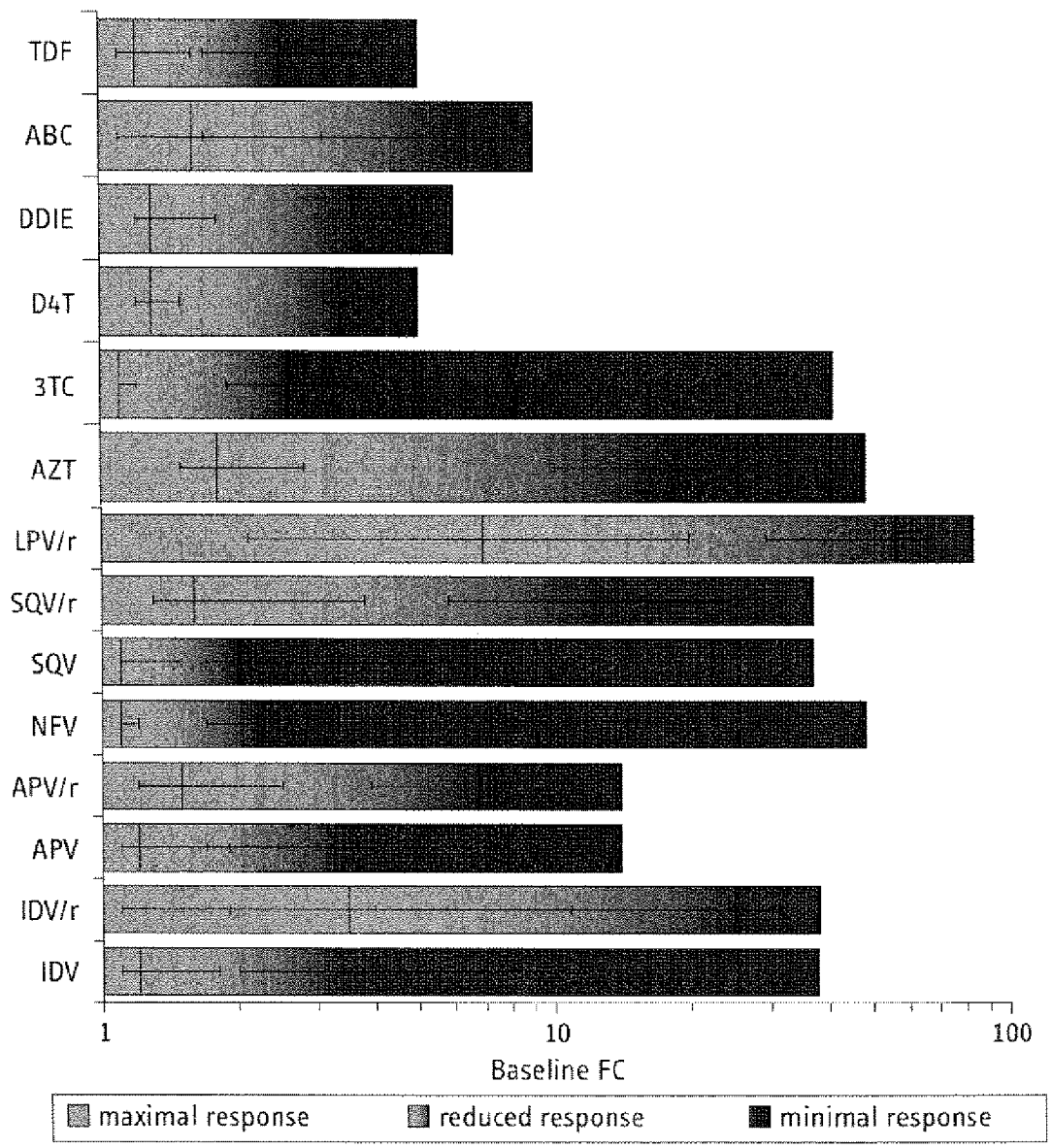
FIG. 9: Example of initial validation of preliminary VirtualPhenotype™ Clinical Cutoffs for nuclesides(tides) and boosted and unboosted protease inhibitors by bootstrapping with 90% confidence intervals.

FIG. 9 shows initial validation of preliminary VirtualPhenotype™ Clinical Cutoffs for nuclesides(tides) and boosted and unboosted protease inhibitors by bootstrapping with 90% confidence intervals.

The problem is tackled from different points of view in order to assess the robustness of the analysis results. The clinical cut-offs obtained could be further refined by adding more data sets and by taking more characteristics of the patients into account. The clinical-cutoffs obtained could also be further refined by performing the model on unseen data.

An alternative method of validation of the model includes calculation of a concordance index (c-index) which describes how all the models can discriminate between patients with a different response. This c-index is calculated on the data set used for model development and on a test data set. If the difference between the two c-indices is small, it means that the models do not lose their predictive ability if applied to new data. The following table contains information regarding the validation procedure for each drug tested when modelled using the preferred embodiment of linear regression which includes the additional factors of sensitivity drug per class in addition to the overall sensitivity score of the background treatment and previous exposure to the drug (e.g. naïve, naïve to PIs, naïve to NRTIs). The test data c-index and the validation data c-index columns relate to the c-indicies for the original test data set and the new data set for validation purposes. The modeled lower and upper values of clinical cutoff are quoted with corresponding confidence intervals.

| | Test Data | | | Validation Data | | | Modelled Lower | Modelled Upper |
|---|---|---|---|---|---|---|---|---|
| Drug | C-index | CCO Odds Ratio | BCO Odds Ratio | C-index | CCO Odds Ratio | BCO Odds Ratio | Cutoff & Confidence Interval | Cutoff & Confidence Interval |
| AZT | 0.79 | 0.065 | 0.107 | 0.78 | 0.252 | 0.316 | 1.9 [1.52-2.76] | 14.4 [8.24-21.20] |
| 3TC | 0.79 | 0.160 | 0.202 | 0.79 | 0.265 | 0.284 | 1.1 [0.98-1.39] | 3.7 [1.71-11.44] |
| D4T | 0.77 | 0.113 | 0.239 | 0.76 | 0.366 | 0.377 | 1.1 [1.05-1.12] | 2.2 [2.05-2.30] |
| DDIE | 0.73 | 0.219 | 0.379 | 0.71 | 0.119 | 0.159 | 1.3 [1.07-1.34] | 3.0 [2.59-2.96] |
| ABC | 0.70 | 0.651 | 0.359 | 0.69 | 0.544 | 0.380 | 0.8 [0.75-1.72] | 1.2 [1.19-5.11] |
| TDF | 0.71 | 0.228 | 0.570 | 0.68 | 0.226 | | 1.0 [0.97-1.32] | 2.0 [1.51-2.95] |
| NVP | 0.79 | 0.282 | 0.290 | 0.83 | 0.054 | 0.054 | 1.5 [1.40-16.74] | 3.2 [2.22-63.06] |
| EFV | 0.79 | 0.079 | 0.099 | 0.79 | 0.041 | 0.042 | 1.8 [1.41-3.74] | 29.2 [6.46-146.69] |
| IDV | 0.76 | 0.098 | 0.194 | 0.79 | 0.270 | 0.598 | 0.8 [0.77-1.04] | 2.2 [1.33-7.19] |
| IDV/r | 0.71 | 0.027 | 0.122 | 0.63 | 0.012 | 0.038 | 4.1 [0.77-6.24] | 21.2 [1.41-22.86] |
| APV | 0.86 | 0.051 | 0.061 | | | | 0.7 [0.65-0.87] | 1.4 [1.03-5.55] |
| APV/r | 0.73 | 0.005 | 0.053 | | | | 0.9 [0.80-2.72] | 6.5 [4.06-16.22] |
| NFV | 0.76 | 0.177 | 0.291 | 0.77 | 1.068 | 0.938 | 1.0 [0.97-1.03] | 1.5 [1.54-2.38] |
| SQV | 0.77 | 0.332 | 0.431 | 0.56 | | | 0.7 [0.65-2.28] | 1.0 [1.03-22.61] |
| SQV/r | 0.71 | 0.165 | 0.249 | 0.81 | 0.054 | 0.080 | 1.1 [0.81-5.98] | 12.0 [4.50-28.85] |
| LPV/r | 0.70 | 0.074 | 0.240 | 0.75 | 0.002 | 0.277 | 10.3 [1.53-17.30] | 61.6 [21.92-66.96] |

The columns headed CCO Odds Ratio and BCO Odds Ratio represent the odds of being a responder in the group that is labeled resistance by the cutoffs divided by the odds of being a responder in the group that is labeled sensitive by the cutoffs. For example, if there are four non-responders and one responder in the resistant group, and four responders and two non-responders in the sensitive group, the odds of being a responder in the resistant group is 1:4=0.25 and the odds of being a responder in the sensitive group is 4:2=2. This means that the odds ratio is 0.25/2=0.125. In other words the odds of being a responder in the resistant group are 0.125 times the odds of being a responder in the sensitive group. The further away that the odds ratio is from 1, the stronger the correlation between the resistance class and clinical outcome.

The separation in groups (resistance/sensitive) can be done based on clinical cutoffs or biological cutoffs. This means that odds ratios based on clinical cutoffs (CCO) and odds ratios based on biological cutoffs (BCO) can be compared. If the odds ratio for the CCO is smaller than the odds ratio for the BCO, it can be concluded that the CCO gives a better prediction than the BCO.

In practice, a logistic regression model is used to determine the odds ratio. The model used is similar to logistic regression model described earlier except that the fold change in the model is replaced by the resistance class. The coefficient for the resistance class that is obtained from the model is the log (odds ratio). The advantage of using this model is that the odds ratio estimates can be adjusted for the baseline viral load and the cPSS score of the background regimen. In one dataset, using the CCOs set out on page 36 herein, the odds ratio for response per additional active drug added was 3.01 when calculated using clinical cutoffs, and 2.32 when calculated using biological cutoffs. These odds ratios are ratios of odds of response for people taking more active drugs over the odds for people taking less active drugs. The odds ratio here should be >1 as the probability of response will increase as the number of active drugs taken increases. In this case, a larger odds ratio indicates a stronger correlation with clinical outcome.

The invention claimed is:

1. A computer-based diagnostic method for estimating for a patient the treatment response of a disease caused by a pathogen to a drug, the method comprising:
   a) inputting data related to the genotype exhibited by a disease causing pathogen to a computer apparatus;
   b) determining, by the computer apparatus, the fold change resistance value of the pathogen infecting the patient;
   c) determining, by the computer apparatus, a clinical cut-off value which is the fold change resistance value at which a clinically relevant variation of clinical response is observed;
   wherein the clinical cut-off value is established by modelling the clinical response of a population of patients treated with the drug to the disease caused by the pathogen as a function of the fold change resistance of the pathogen infecting the patients;
   d) comparing, by the computer apparatus, the fold change resistance value of the pathogen infecting the patient to the clinical cut-off value;
   e) calculating, by the computer apparatus, the predicted treatment response of a disease caused by the pathogen, and
   f) outputting the results of the computer-generated estimate of the treatment response.

2. A method according to claim 1, wherein the cut-off value is determined as a function of treatment response data in treated subjects, considering baseline pathogen load, baseline fold change resistance and baseline activity of coadministered drugs targeted to the pathogen.

3. A method according to claim 1, wherein the cut-off value is calculated by reference to the pathogen load drop.

4. A method according to claim 3, wherein the cut-off value is calculated by reference to the log pathogen load drop.

5. A method according to claim 4, wherein the log pathogen load drop is calculated by performing a linear regression analysis using data from a dataset of treatment response data, wherein the log pathogen load drop LogPL $drop_i$, for the pathogen infecting a patient i, is modelled as the sum of all of the individual contributions for factors that influence pathogen load drop, according to the following equation:

$$\text{LogPLdrop}_i = \beta_0 + \beta_1 \text{Log}(\text{BaselinePL}_i) + \beta_2(\text{PSS}_i) + \beta_3(1/\text{FC}_i) + \epsilon_i$$

wherein BaselinePL$_i$ represents the pathogen load of the patient measured at the start of treatment by the drug, PSS$_i$ is a phenotypic sensitivity score representing the number of active drugs in the background treatment regimen for the patient, excluding the drug whose contribution to treatment response is being modelled, FC$_i$ is a baseline fold change resistance, $\beta_0$ is the intercept, $\beta_1$ is a coefficient representing the increase in log pathogen load drop per unit increase of the log of the BaselinePL$_i$, $\beta_2$ is a coefficient indicating the increase in log pathogen load drop per unit increase of the number of sensitive drugs in the background treatment regimen, $\beta_3$ is a coefficient indicating the increase in log pathogen load drop per unit increase of the inverse of FC$_i$, and wherein the error term, $\epsilon_i$, represents the difference between the modelled prediction and the experimentally determined measurement.

6. A method according to claim 4, wherein the log pathogen load drop is calculated by performing a linear regression analysis using data from a dataset of treatment response data, wherein the log pathogen load drop LogPL $drop_i$, for the pathogen infecting a patient i, is modelled as the sum of all of the individual contributions for factors that influence pathogen load drop, according to the following equation:

$$\text{LogPLdrop}_i = \beta_0 + \beta_1 \text{Log}(\text{BaselinePL}_i) + \beta_2(\text{cPSS}_i) + \beta_3(\text{cPSS}_i)^2 + \beta_4(\text{FC}_i)^p + \beta_5(H_5) + \ldots + \beta_n(H_n) + \epsilon_i$$

wherein the terms of the equation are the same as those given in claim 5, and additionally, p is a power transformation (e.g. ranging from −3 to 1) and $H_5$ to $H_n$ are treatment history parameters or parameters describing the background therapy as a function of a certain therapeutic class.

7. A method according to claim 1, wherein the cut-off response value is calculated by reference to the probability of the pathogen being susceptible to treatment by the drug for the patient, herein termed Prob of success.

8. A method according to claim 7, wherein Prob of success is calculated by performing a logistic regression analysis using data from a dataset of treatment response data, wherein Prob of success is modelled according to the following equation:

$$\text{Prob of success} = \frac{\exp\left(\beta_0 + \beta_1 \text{Log}(\text{BaselinePL}_i) + \beta_2(\text{PSS}_i) + \beta_3(1/FC_i)\right)}{1 + \exp\left(\left(\beta_0 + \beta_1 \text{Log}(\text{BaselinePL}_i) + \beta_2(\text{PSS}_i) + \beta_3(1/FC_i)\right)\right)}$$

wherein BaselinePL$_i$ represents the pathogen load of the patient measured at the start of treatment by the drug, PSS$_i$ is a phenotypic sensitivity score representing the number of active drugs in the background treatment regimen for the patient, excluding the drug whose contribution to treatment response is being modelled, FC$_i$ is a baseline fold change resistance, $\beta_0$ is the intercept, $\beta_1$ is a coefficient representing the increase in log pathogen load drop per unit increase of the log of the BaselinePL$_i$, $\beta_2$ is a coefficient indicating the increase in log pathogen load drop per unit increase of the number of sensitive drugs in the background treatment regimen, and $\beta_3$ is a coefficient indicating the increase in log pathogen load drop per unit increase of the inverse of FC$_i$.

9. A method according to claim 1, wherein the cut-off fold change resistance value is calculated by reference to the likelihood of a patient achieving treatment success or failure, where a definition of success is having an undetectable pathogen load after treatment with a particular drug, using a classification tree.

10. A method according to claim 9, wherein the clinical cut-off value is defined as the fold change resistance threshold value that makes the best distinction between the population with successful treatments and the population with unsuccessful treatments.

11. A method according to anyone of the preceding claims, wherein the baseline fold change resistance is determined by comparing the genotype of the disease causing pathogen to phenotype data collected from a group of patients infected with a pathogen of similar genotype.

12. A method according to claim 11, wherein the baseline fold change resistance is determined by predicting the drug resistance phenotype of a pathogen genotype.

13. A method according to claim 1, that incorporates two or more of the methods of calculating the cut-off value by i) reference to the log pathogen load drop wherein the log pathogen load drop is calculated by:

a) performing a linear regression analysis using data from a dataset of treatment response data, wherein the log pathogen load drop LogPL $drop_i$, for the pathogen infecting a patient i, is modelled as the sum of all of the individual contributions for factors that influence pathogen load drop, according to the following equation:

$$\text{LogPLdrop}_i = \beta_0 + \beta_1 \text{Log}(\text{BaselinePL}_i) + \beta_2(\text{PSS}_i) + \beta_3(1/\text{FC}_i) + \epsilon_i$$

wherein BaselinePL$_i$ represents the pathogen load of the patient measured at the start of treatment by the drug, PSS$_i$ is a phenotypic sensitivity score representing the number of active drugs in the background treatment regimen for the patient, excluding the drug whose contribution to treatment response is being modelled, FC$_i$ is a baseline fold change resistance, $\beta_0$ is the intercept, $\beta_1$ is a coefficient representing the increase in log pathogen load drop per unit increase of the log of the BaselinePL$_i$, $\beta_2$ is a coefficient indicating the increase in log pathogen load drop per unit increase of the number of sensitive drugs in the background treatment regimen, $\beta_3$ is a coefficient indicating the increase in log pathogen load drop per unit increase of the inverse of FC$_i$, and wherein the error term, $\epsilon_i$, represents the difference between the modelled prediction and the experimentally determined measurement, or b) performing a linear regression analysis using data from a dataset of treatment response data, wherein the log pathogen load drop LogPL drop$_i$, for the pathogen infecting a patient i, is modelled as the sum of all of the individual contributions for factors that influence pathogen load drop, according to the following equation:

$$\text{LogPLdrop}_i = \beta_0 + \beta_1 \text{Log}(\text{BaselinePL}_i) + \beta_2(\text{cPSS}_i) + \beta_3(\text{cPSS}_i)^2 + \beta_4(\text{FC}_i)^p + \beta_5(H_5) + \ldots + \beta_n(H_n) + \epsilon_i$$

wherein p is a power transformation (e.g. ranging from −3 to 1), and $H_5$ to $H_n$ are treatment history parameters or parameters describing the background therapy as a function of a certain therapeutic class;

or ii) reference to the probability of the pathogen being susceptible to treatment by the drug for the patient, herein termed Prob of success wherein Prob of success is calculated by performing a logistic regression analysis using data from a dataset of treatment response data, wherein Prob of success is modelled according to the following equation:

$$\text{Prob of success} = \frac{\exp(\beta_0 + \beta_1 \text{Log}(\text{Baseline}PL_i) + \beta_2(PSS_i) + \beta_3(1/FC_i))}{(1 + \exp(\beta_0 + \beta_1 \text{Log}(\text{Baseline}PL_i) + \beta_2(PSS_i) + \beta_3(1/FC_i)))};$$

and calculating the cut-off fold change resistance value by reference to the likelihood of a patient achieving treatment success or failure, where a definition of success is having an undetectable pathogen load after treatment with a particular drug, using a classification tree.

14. A method according to claim 1, wherein the disease causing pathogen is obtained from a patient sample chosen from a blood sample, a biopsy sample, a plasma sample, a saliva sample, a tissue sample, and a bodily fluid or mucous sample.

15. A method according to claim 1, wherein the disease causing pathogen is a virus.

16. A method according to claim 15, wherein the disease causing virus is chosen from HIV, HCV and HBV.

17. A method according to claim 1, wherein the method is performed for a number of candidate drugs so as to provide information on the predicted fold resistance exhibited by the pathogen to a spectrum of candidate drugs.

18. A diagnostic method for optimising a drug therapy in a patient, comprising performing a method according to claim 1 for each drug or combination of drugs being considered to obtain a series of drug resistance phenotypes and therefore assess the effect of the plurality of drugs or drug combinations on the pathogen with which the patient is infected and selecting the drug or drug combination for which the pathogen is predicted to have the lowest fold resistance.

19. A method according to claim 1 further comprising assessing the efficiency of the patient's therapy, evaluating a therapy or optimizing a therapy.

20. A computer-based diagnostic system for predicting clinical response to a drug of a disease causing pathogen comprising: a) means for obtaining a genetic sequence of the disease producing pathogen; b) means for identifying at least one mutation in the genetic sequence of the disease producing pathogen; c) genotype database means comprising genotype entries; d) phenotype database means comprising phenotypes of patient fold change response values; e) clinical response database means comprising clinical response to drug treatment for reference sample patients; f) correlation means correlating a genotype entry with a phenotype, where the genotype entry corresponds with the obtained genetic sequence of the disease producing pathogen; g) means for modelling clinical response to a drug of the disease causing pathogen by determining whether the patient fold change response is above a cut-off value, wherein the cut-off value is determined using the clinical response database means and comprises the fold change response value at which a clinically relevant diminished clinical response is observed; h) means for predicting the clinical response to a drug of a disease by determining whether the patient fold change response is above the cut-off value; and i) means for generating an output of the predicted clinical response to a drug of a disease causing pathogen.

21. A diagnostic system according to claim 20, wherein the cut-off value is determined as a function of treatment response data in treated subjects, considering baseline pathogen load, baseline fold change resistance, baseline activity of co-administered drugs targeted to the pathogen and treatment history.

* * * * *